United States Patent [19]
Vandekerckhove et al.

[11] Patent Number: 5,623,067
[45] Date of Patent: Apr. 22, 1997

[54] SEED-SPECIFIC PROMOTER REGION

[75] Inventors: Joël S. Vandekerckhove, Loppem, Belgium; Enno Krebbers, Alhambra, Calif.; John Botterman, Zevergem-de Pinte; Jan Leemans, Deurle, both of Belgium

[73] Assignees: Plant Genetic Systems, N.V., Ghent, Belgium; Brazilian Agricultural Research Organization-Embrapa/Cenargen, Brasilia, Brazil

[21] Appl. No.: 459,942

[22] Filed: Jun. 2, 1995

Related U.S. Application Data

[62] Division of Ser. No. 45,773, Apr. 14, 1993, Pat. No. 5,487,991, which is a continuation of Ser. No. 363,898, filed as PCT/EP88/00944, Oct. 20, 1988, abandoned.

[30] Foreign Application Priority Data

Oct. 20, 1987 [GB] United Kingdom ................. 87402348

[51] Int. Cl.$^6$ ............................ C12N 15/11; C12N 15/29; C12N 15/82
[52] U.S. Cl. ................. 536/24.1; 435/172.3; 435/320.1; 800/205
[58] Field of Search ....................... 536/24.1; 435/240.4, 435/172.3, 320.1; 800/205

[56] References Cited

U.S. PATENT DOCUMENTS

| | | | |
|---|---|---|---|
| 4,617,149 | 10/1986 | DiMarchi et al. | 530/324 |
| 4,886,878 | 12/1989 | Larkins et al. | 536/26 |
| 4,956,282 | 9/1990 | Goodman et al. | 435/69.51 |
| 5,003,045 | 3/1991 | Hoffman | 530/378 |

FOREIGN PATENT DOCUMENTS

| | | |
|---|---|---|
| 0067553 | 12/1982 | European Pat. Off. |
| 0142924 | 5/1985 | European Pat. Off. |
| 0208418 | 1/1987 | European Pat. Off. |
| 0255378 | 2/1988 | European Pat. Off. |
| 240911 | 11/1986 | Germany |
| 2068971 | 8/1981 | United Kingdom |
| 83/01176 | 4/1983 | WIPO |
| 87/00865 | 2/1987 | WIPO |
| 87/07299 | 12/1987 | WIPO |

OTHER PUBLICATIONS

Josefsson et al 1987 (Sep. 5) J of Biol. Chem. 262(25):12196–12201.
Krebbers et al 1988 (Aug.) Pl. Physiol 87(4):859–866.
Conceicao et al 1994 The Plant Journal 5(4):493–505.
Guerche et al 1990 The Plant Cell 2:469–478.
Radke et al., Theor. Appl. Genet., vol. 75, pp. 685–694 (1988).
Schwenke et al., Biochem. Physiol. Pflanzen, vol. 183, pp. 219–224 (1988).
Sambrook et al., "Molecular Cloning," Cold Spring Harbor Laboratory Press, 1989.
Vandekerckhove et al., 1989 Bio/Tech 7:929–932.
Ma et al., 1980, pl Physical 66:897–902.
Messing et al., 1983, In Genetic Engineerings of Plants, Kosuse et al., (ed) Plenum Press pp. 211–227.
Nielsen 1985, In World Soybean Research Conf III: Proceedings Shibles (ed) Westview Press, pp. 281–290.
Forde et al., 1985, The EMBO J 4:9–15.
Donaldson et al., J. of Cell. Biochem., vol. 0, No. 10, part d p. 53, abstract N137 (1986).
Altenbach et al., Plant Molecular Biology, vol. 8, No. 3, pp. 239–250 (1987).
Slightom and Chee, Biotech. Adv., vol. 5, pp. 29–45 (1987).
Okamura et al., Proc. Natl. Acad. Sci. USA, vol. 83, pp. 8240–8244 (1986).
Sengupta–Gopalan et al., Proc. Natl. Acad. Sci. USA, vol.82, pp. 3320–3324 (1985).
Dickinson et al., Proc. Natl. Acad. Sci. USA, vol. 84, pp. 5525–5529 (1987).
Kempe et al., Bio/Technology, vol. 4, pp. 565–568 (1986).
Scofield and Crouch, J. of Biolog. Chem., vol. 262, No. 25, pp. 12202–12208 (1987).
Radke et al., Biological Abstracts, vol. 86, No. 4, 34125 (1988).
Krebbers et al., Biological Abstracts, vol. 86, No. 12, 124569 (1988).
Altenbach et al., J. of Cell. Biochem., Suppl. 12C, p. 177, abstract L 300 (1988).
Altenbach et al., J. of Cell. Biochem., Suppl. 12C, vol. 0, No. 11, part B, p. 46, abstract F401 (1987).
Jaynes et al., Trends in Biotechnology, vol. 4, pp. 314–320, 1986.

*Primary Examiner*—Patrick R. Moody
*Attorney, Agent, or Firm*—Keck, Mahin & Cate

[57] ABSTRACT

A seed-specific promoter is described which is obtained from an Arabidopsis seed storage protein gene encoding 2S albumin.

3 Claims, 25 Drawing Sheets

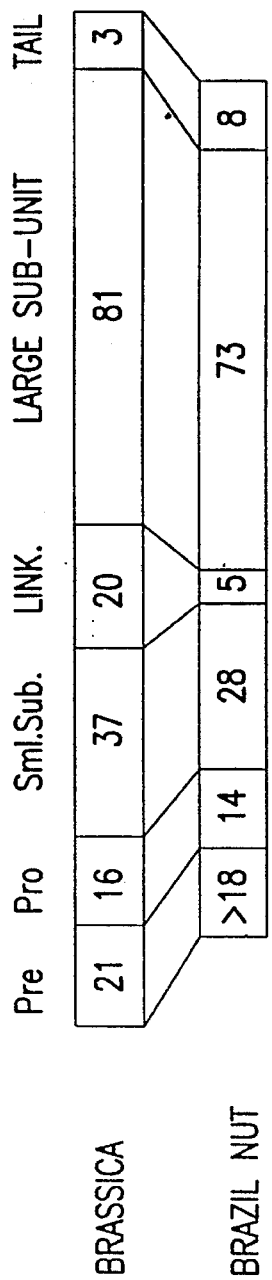

Small Subunit

```
R. comm.         P - S Q Q G C R G Q I Q E Q Q N L R Q C Q E
B. exce.     - - - - - - Q E E C R E Q M Q R Q Q M L S H C R M
B. napus   S A G P F R I P K C R K E F Q Q A Q H L R A C Q Q
A. thali.  P I G P K M R - K C R K E F Q K E Q H L R A C Q Q
```

```
R. comm.   Y I - K Q Q V - S G Q G P R R                    (34)
B. exce.   Y M R Q Q M E E S                                (28)
B. napus.  W L H K Q A M Q S G                              (35)
A. thali.  L M L Q Q A R Q - G R S D                        (36)
```

Large Subunit

```
R. comm.           Q E R - S L R G C C D H L K Q M Q - S Q
B. excel.  P R R G M E P H M S E - - C C E Q L E G M D E S -
B. napus.  P Q G P Q Q R P P L L Q Q C C N E L H Q - - E E P
A. thali   P Q G Q Q Q E Q Q L F Q Q C C N E L R Q - - E E P
```

```
R. comm.   - C R C E G L R Q A - - - - - - - I Q Q Q - Q L Q
B. excel.  - C R C E G L R M M M M R M Q Q E E M - Q P R - -
B. napus.  L C V C P T L K G A S K A V K Q Q I Q Q Q G Q Q Q
A. thali.  D C V C P T L K Q A A K A V R L Q G Q H Q - P M Q
```

```
R. comm.   G - - Q N V F E A F R T A A N L P S M C G V S P T
B. excel   G E - Q M - R R M M R L A E N I P S R C N L S P M
B. napus.  G K Q Q M V S R I Y Q T A T H L P K V C N I - P Q
A. thali.  - - - - - V R K I Y Q T A K H L P N V C D I - P Q
```

```
R. comm.   Q - - C R F                                      (61)
B. excel.  R - - C P M G G S                                (73)
B. napus.  V S V C P F Q K T M P G - P S                    (86)
A. thali.  V D V C P F N - - I P S F P S                    (79)
```

FIG. 2

Signal peptide

| | | |
|---|---|---|
| B. exce. | N A K I S V A A A A L L V L N A L G N A T A | (12) |
| B. napus. | N A N K L F L V S A T L A F - F F L L T N A | (21) |
| AT251 | N A N K L F L V C A A L A L - C F L L T N A | (21) |
| AT252 | N A N K L F L V C A T F A L - C F L L T N A | (**) |
| AT253 | N A N K L F L V C A T L A L - C F L L T N A | (**) |
| AT254 | N A N K L F L V C A A L A L - C F I L T N A | (**) |

Amino Terminal Processed Fragment

| | | |
|---|---|---|
| B. exce. | - F R A T V T T T V V - E E E N | (14) |
| B. napus | S I Y A T V V E F D E D D A T N | (16) |
| AT251 | S I Y R T V V E F E E D D A T N | (18) |
| AT252 | S I Y R T V V E F D E D D A S N | (**) |
| AT253 | S I Y R T V V E F E E D D A S N | (**) |
| AT254 | S V Y R T V V E F D E D D A S N | (**) |

Small subunit

| | |
|---|---|
| R. comm. | P - S Q Q C R G Q I Q E Q Q N L R C C Q E |
| B. exce. | - - - - - - Q E E C R E Q M Q R Q Q M L S N C R N |
| B. napus. | S A G P F R I P R C R K E F Q Q A Q N L R A C Q Q |
| AT251 | F I G P K N R - K C R K E F Q K E Q N L R A C Q C |
| AT252 | P H G P - - R Q K C Q K E F Q Q S Q N L R A C Q K |
| AT253 | P V G P - - R Q R C Q K E F Q Q S Q N L R A C Q K |
| AT254 | P I G P - - I Q K C Q K E F Q Q D Q N L R A C Q R |

| | | |
|---|---|---|
| R. comm. | Y I - K Q Q V - S G Q G P R K | (34) |
| B. exce. | T N R Q Q H E E S | (26) |
| B. napus | N L N K Q A M Q S G | (35, 29) |
| AT251 | L H L Q Q A R Q - G R S D | (36) |
| AT252 | L H K M Q N R Q - G R G G | (**) |
| AT253 | N H S K Q N R Q - G R G G | (**) |
| AT254 | N H R K Q N W Q - G R G G | (**) |

FIG. 2A

Internal Processed Fragment

```
B. excel.    P Y Q T N                              ( 5)
B. napus     G G F N M T L D G E F D F E D D M E N  (19)
AT251        - - - - - - - - - E F D F E D D M E N  (10)
AT252        - G P - - S L D D E F D L E D D I E N  (**)
AT253        - G P - - S L D D E F D                (**)
AT254        - G P - - S L D D E F D N E D D I E N  (**)
```

Large Subunit

```
                              * *
R. comm.         Q E R - S L R G C C D N L K Q N Q - S Q
B. excel.    F R R G M E F N M S E - - C C E Q L E G N D E S -
B. napus     P Q G F Q Q R F P L L Q Q C C N E L N Q - - E E F
AT251        P Q G Q Q Q E Q Q L F Q Q C C N E L R Q - - E E F
AT252        P Q G P Q Q G N Q I L Q Q C C S E L R Q - - E E F
AT253        F E G P Q Q G Y Q L L Q Q C C N E L R Q - - E E F
AT254        F - - - - Q R R Q L L Q K C C S E L R Q - - E E F
```

```
              * *
R. comm.     - C R C E G L R Q A - - - - - - - I Q Q Q - Q L Q
B. excel.    - C R C E G L R N N N N R N Q Q E E N - Q P R - -
B. napus     L C V C P T L K G A S K A V K Q Q I Q Q Q G Q Q Q
AT251        D C V C P T L K Q A A K A V R L Q G Q - N Q P M Q
AT252        V C V C P T L R Q A A R A V S L Q G Q - N G P F Q
AT253        V C V C P T L K Q A A R A V S L Q G Q - N G P F Q
AT254        V C V C P T L R Q A A K A V R F Q G Q Q N Q P E Q
```

```
                                            *
R. comm.     G - - Q N V F E A F K T A A N L P S M C G V S P T
B. excel.    G E - Q M - R R M M R L A E N I P S R C N L S P N
B. napus     G K Q Q M V S R I Y Q T A T N L P K V C N I - F Q
AT251        - - - - - V R K I Y Q T A K N L P N V C D I - F Q
AT252        - - - - - S R K I Y K T A K Y L P N I C K I - Q Q
AT253        - - - - - S R K I Y Q S A K Y L P N I C K I - Q Q
AT254        - - - - - V R K I Y Q A A K Y L P N I C K I - Q Q
```

FIG.2B

| | | |
|---|---|---|
| R. comm. | Q - - C R F | (61) |
| B. excel. | R - - C P M G G S | (73) |
| B. napus | V S V C P F Q K T M F G - F S | (86) |
| AT251 | V D V C P F N - - I P S F P S | (79) |
| AT252 | V G E C P F Q T T I P F F P P | (**) |
| AT253 | V G E C P F Q T T I P F F P P | (**) |
| AT254 | V G V C P F Q - - I P S T P S | (**) |

Carboxyl Terminal Processed Fragment

| | | |
|---|---|---|
| B. excel. | I A G F | ( 4) |
| B. napus | I - | ( 1) |
| AT251 | F I | ( 2) |
| AT252 | Y - | (**) |
| AT253 | Y Y | (**) |
| AT254 | Y Y | (**) |

FIG.2C

```
linker  A  A  A  A  L  L  V  L  M  A  L  G  H  A  T  A  F  R   18
GAATTCCGCGGCAGCAGCCCTCCTTGTCCTCATGGCCCTCGGCCACGCCACCGCCTTCCG   60
Eco RI                                                Bgl I
                                        *Start mature small subunit
        A  T  V  T  T  T  V  V  E  E  N *Q  E  E  C  R  E  Q  M  38
GGCCACCGTCACCACCACAGTGGTGGAGGAGGAGAACCAGGAGGAGTGTCGCGAGCAGAT  120

Q  R  Q  Q  M  L  S  H  C  R  M  Y  M  R  Q  Q  M  E  E  S  58
GCAGAGACAGCAGATGCTCAGCCACTGCCGGATGTACATGAGACAGCAGATGGAGGAGAG  180

*  Processed   *Large subunit  ——▶
       *P  Y  Q  T  M* P  R  R  G  M  E  P  H  M  S  E  C  C  E  Q  78
CCCGTACCAGACCATGCCCAGGCGGGGAATGGAGCCGCACATGAGCGAGTGCTGCGAGCA  240

L  E  G  M  D  E  S  C  R  C  E  G  L  R  M  M  M  M  R  M  96
GCTGGAGGGGATGGACGAGAGCTGCAGATGCGAAGGCTTAAGGATGATGATGATGAGGAT  300
                         PstI

Q  Q  E  E  M  Q  P  R  G  E  Q  M  R  R  M  M  R  L  A  E 118
GCAACAGGAGGAGATGCAACCCCGAGGGGAGCAGATGCGAAGGATGATGAGGCTGGCCGA  360
GCAACAGGAGAAGTACGGTGGATTCTTGAAGCAGATGCG-3' oligonucleotide
        K  Y  G  G  F  L  K
                                              End mat. lg. su.*
        N  I  P  S  R  C  N  L  S  P  M  R  C  P  M  G  G  S* I  A 136
GAATATCCCTTCCCGCTGCAACCTCAGTCCCATGAGATGCCCCATGGGTGGCTCCATTGC  420

G  F  *                                                    140
CGGGTTCTGAATCTGCCACTAGCCAGTGCTGTAAATGTTAATAAGGCTCTCACAAACTAG  480

EcoRI  polylinker——▶
CTCTTTGTTGGCTTTTTGGCCGGAGACTAGGGTGTGGGGAATTCGAGCTCGGTACCCGGGG  540

PstI
ATCCTCTAGAGTCGACCTGCAGGCATGCAAGCTT                             574
```

FIG.4

```
pLe 1
   A    N  *  S    A
  GCA  AAC  TCA  GCG
  CGT  TTG  AGT  CGC
           DdeI
           C/TNAG pSOYLEA 1
   A    N  *  S    D    L
  GCA  AAC  TCA  GAT  CTG
  CGT  TTC  AGT  CTA  GAC
                BglII
                A/GATCT
pBN2S1
   T    A  *  F    R    A    T
  ACC  GCC  TTC  CGG  GCC  ACC
  TCC  CGG  AAG  GCC  CGG  TGG
           BglI
           GCCNNNN/NGGC
```

FIG.5

```
P  Q  G  Q  Q  Q  E  Q  Q  L  F  Q  Q  C  C  N  E  L  R  Q  E
GGICAICAICAIGAICAICAIITITTICAICAITGITGIAAIGA

E  P  D  C  V  C  P  T  L  K  Q  A  A  K  A  V  R  L  Q  G  Q
                    AAICAIGCIGCIAAIGCIGTIIGIITICAIGGICAI

H  Q  P  M  Q  V  R  K  I  Y  Q  T  A  K  H  L  P  N  V  C  D
CAICA                                          CCIAAIGTITGIGAI

I  P  Q  V  D  V  C  P  F  N  P
ATICCICAIGTIGAIGTITGICCITTIAAICC
```

FIG.14

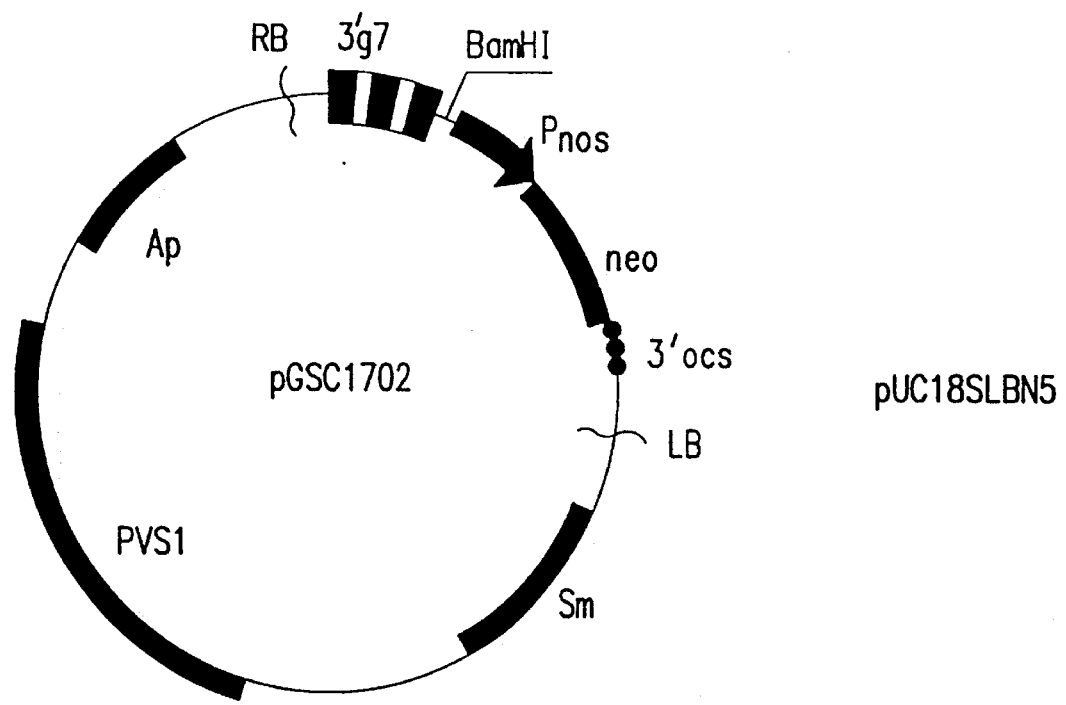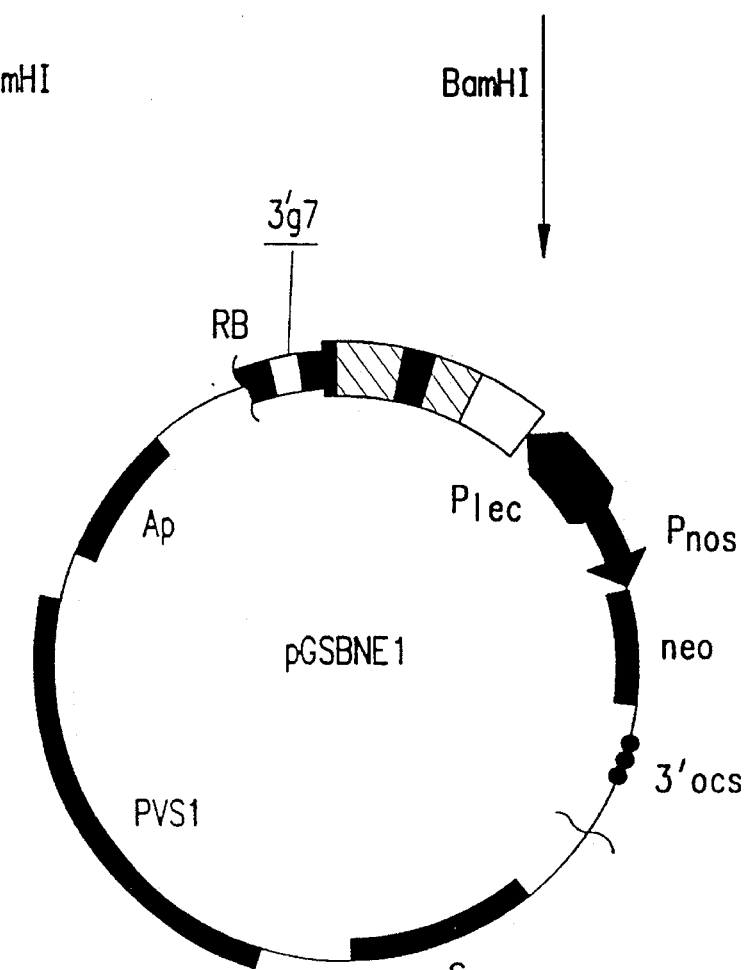
FIG.12

```
                                                     ATCTTTATCCA  -421
TATATTGTCTTACCATCAATAGACAATATCCAATGGACCGGTGACCTGCGTGTATAAGTA     -361
ATTTTTCAAGATGCTAAAACTTTTATGTATTTCAGAATTAACCTCCAAAAACATTTATTG     -301
ACACACTACTACTCTTTCCGTATTGACTCTCAACTAGTCATTTCAAAATAATTGACATGT     -241
CAGAACATGAGTTACACATGGTTGCATATTGCAAGTAGACGCGGAAACTTGTCACTTCCT    -181
TTACATTTGAGTTTCCAACACCTAATCACGACAACAATCATATAGCTCTCGCATACAAAC    -121
AAACATATGCATGTATTCTTACACGTGAACTCCATGCAAGTCTCTTTTCTCACCTATAAA     -61
TACCAACCACACCTTCACCACATTCTTCACTCGAACCAAAACATACACACATAGCAAAAA     -1

M  A  N  K  L  F  L  V  C  A  A  L  A  L  C  F  L  L  T  N   20
    ATGGCAAACAAGTTGTTCCTCGTCTGCGCAGCTCTCGCTCTCTGCTTCCTCCTCACCAAC    60
                                                 *Start SSU
     A  S  I  Y  R  T  V  V  E  F  E  E  D  D  A  T  N* P  I  G    40
    GCTTCCATCTACCGCACCGTCGTTGAGTTCGAAGAAGATGACGCCACTAACCCCATAGGC   120

P  K  M  R  K  C  R  K  E  F  Q  K  E  Q  H  L  R  A  C  Q    60
    CCAAAAATGAGGAAATGCCGCAAGGAGTTTCAGAAAGAACAACACCTAAGAGCTTGCCAG   180
                                              *Processed——►
     Q  L  M  L  Q  Q  A  R  Q  G  R  S  D *E  F  D  F  E  D  D    80
    CAATTGATGCTCCAGCAAGCAAGGCAAGGCCGTAGCGATGAGTTTGATTTCGAAGACGAC   240
               * Large subunit——►
     M  E  N *P  Q  G  Q  Q  Q  E  Q  Q  L  F  Q  Q  C  C  N  E   100
    ATGGAGAACCCACAGGGACAACAGCAGGAACAACAGCTATTCCAGCAGTGCTGCAACGAG   300

L  R  Q  E  E  P  D  C  V  C  P  T  L  K  Q  A  A  K  A  V   120
    CTTCGCCAGGAAGAGCCAGATTGTGTTTGCCCCACCTTGAAACAAGCTGCCAAGGCCGTT   360
                             oligonucleotide 5' - CAAGCTGCCAAGTACGGT
                                                           K  Y  G R  L  Q  G  Q  H  Q  P  M  Q  V  R  K  I  Y  Q  T  A  K  H   140
    AGACTCCAGGGACAGCACCAACCAATGCAAGTCAGGAAAATTTACCAGACAGCCAAGCAC   420
    GGATTCTTGAAGCAGCACCAAC-3' oligo
     G  F  L  K
                                              End mat. lg. su.*
     L  P  N  V  C  D  I  P  Q  V  D  V  C  P  F  N I* P  S  F    160
    TTGCCCAACGTTTGCGACATCCCGCAAGTTGATGTTTGTCCCTTCAACATCCCTTCATTC   480

P  S  F  Y  *                                                 164
    CCTTCTTTCTACTAAATCTCAAACAAACCCTCAAAGCCGTATGAGAGTGTGGTTGTTGATA  540

TATACATGTTGACACTTGACACATACCACACCTCATCGTGTGTTTTATGATAAATGT      597
```

FIG.13

```
                        1
         M  Y  A  D  A  I  F  T  N  S  Y  R  K  V  L  G  Q  L*
    GATCCATGTACGCTGATGCAATATTCACCAACTCTTACAGGAAGGTCCTAGGCCAACTCA
    GTACATGCGACTACGTTATAAGTGGTTGAGAATGTCC|TTCCAGGATCCGGTTGAGT
                        5
              |     6       |                        2,4
    S* A  R  K|L  L  Q  D|I  L  S  R  Q  Q  G  E  S  N  Q  E
    GCGCTAGAAAATTGCTCCAAGACATCCTCTCACGCCAGCAGGGAGAATCCAACCAGGAGA
    CGCGATCTTTTAACGAGGTTCTGTAGGAGAGTGCGGTCGTCCCTCTTAGGT|TGGTCCTCT
          3                                                  |

R  G  A  R  A  R |L  G |M
    GAGGCGCCCCGCGCTAGG|TTGGGA|ATGATCTGCA
    CTCCGCGGGGCGCGATCC|AACCCT|TACTAG
     7,8
```

FIG.22A

```
                  K    G    I    H
                 AAA  GGT'AT  A   CAC
                 TTT  CCA  TA'T   GTG

K    G    I    M    Y                         G    M    I    I    H
    AAA  GGT  ATC  ATG  TAC   — PEPTIDE —         GGA  ATG  ATC  ATA  CAC
    TTT  CCA  TAG  TAC  ATG   — SEQUENCE —        CCT  TAC  TAG  TAT  GTG
```

FIG.22B

SEED-SPECIFIC PROMOTER REGION

This application is a divisional of Ser. No. 08/045,773, filed 14 Apr. 1993 (now U.S. Pat. No. 5,487,991), which is a continuation of Ser. No. 07/363,898, filed 2 Aug. 1989 (now abandoned), which is a national stage application of PCT/EP88/00944 filed 20 Oct. 1988.

The invention relates to a process for the production of useful biologically active polypeptides through the modification of appropriate plant genes.

The production of determined biologically active polypeptides in easily purifiable form and useful quantities is still fraught, in most instances, with considerable difficulties.

Alternative procedures are chemical synthesis or production by genetically engineered microorganisms. The first is very expensive and often does not result in polypeptides with the correct conformation. The latter alternative is difficult due to problems of instability of the polypeptide, intracellular precipitation, and purification of the product in a pure form. In addition, some classes of peptides, including hormonal peptides, are fully active only after further processing such as correct disulfide bridge formation, acetylation, glycosylation or methylation. In nature disulfide bridges are formed with high efficiency because they are co-translationally catalysed by protein disulfide isomerase during membrane translocation of the precursors. The active form is then derived from the precursor by proteolytic cleavage processes.

Peptides chemically synthesised or overproduced in prokaryotic systems are generally obtained in a reduced form, and the disulfide bridges must then be formed by mild oxidation of the cysteine residues. Since one often starts from the fully denatured "scrambled" state of the peptide, disulfide bridge formation is then a random process, during which intermolecular bridges (yielding higher molecular weight aggregates) and incorrect disulfide bonds (yielding inactive peptides) may be generated in addition to the correctly folded peptide.

Using plant cells as systems for the production of determined peptides has also been suggested, e.g. in PCT/US86/01599. There is no evidence in that patent that the suggested methods, whose principle lies in bringing constitutively to expression said peptide according to known techniques (EP83112985.3), permit obtaining high expression levels without disturbing the plant physiology and high yields in recovering said peptides by separating them from plant proteins. This will especially be the case when the whole plant is used as such and grown in soil.

An object of the invention is to overcome these difficulties, to provide economically valuable processes and genetically engineered live matter which can be produced in large amounts, in which determined polypeptides can both be synthesized in large amounts without disturbing the physiology of said live matter and produced in a form providing for a high degree of physiological activity common to the wild type peptide having the same or substantially the same amino acid sequences and can be easily recovered from said live matter.

More particularly the invention aims at providing genetically modified plant DNA and plant live material including said genetically modified DNA replicable with the cells of said plant material, which genetically modified plant DNA contains sequences encoding for said determined polypeptides whose expression is under the control of a given plant promotor which conducts said expression in at least a stage of the development of the corresponding plants. This stage of development is chosen in a way that the expression occurs in plant organs or tissue which are produced in high amounts and easily recoverable.

A further object of the invention is to take advantage of the capacity of seed storage proteins to be produced in large amounts in plants and to be expressed at a determined stage of development of said plants, particularly at the seed formation stage. More particularly the invention aims at taking advantage of the ease with which water soluble storage proteins can be recovered from the corresponding plant seeds.

The expression of foreign genes in plants is well established (De Blaere et al., 1987). In several cases seed storage protein genes have been transferred to other plants. In several cases it was shown that within its new environment the transferred seed storage protein gene is expressed in a tissue specific and developmentally regulated manner (Beachy et al., 1985; Okamuro et al., 1986; Sengupta-Gopalan et al., 1985; Higgins et al., 1986). This means that the transferred gene is expressed only in the appropriate parts of the seed, and only at the normal time. It has also been shown in at least one case that foreign seed storage proteins are located in the protein bodies of the host plant (Greenwood and Chrispeels, 1985). It has further been shown that stable and functional messenger RNAs can be obtained if a cDNA, rather than a complete gene including introns, is used as the basis for the chimeric gene (Chee et al., 1986).

Seed storage proteins represent up to 90% of total seed protein in seeds of many plants. They are used as a source of nutrition for young seedlings in the period immediately after germination. The genes encoding them are strictly regulated and are expressed in a highly tissue specific and stage specific fashion ((Walling et al., 1986; Higgins, 1984). Thus they are expressed almost exclusively in developing seed, and different classes of seed storage proteins may be expressed at different stages in the development of the seed. They are generally restricted in their intracellular location, being stored in membrane bound organelles called protein bodies or protein storage vacuoles. These organelles provide a protease-free environment, and often also contain protease inhibitors. These proteins are degraded upon flowering, and are thought to serve as a nutritive source for developing seeds. Simple purification techniques for several classes of these proteins have been described.

Seed storage proteins are generally classified on the basis of solubility and size (more specifically sedimentation rate, for instance as defined by Svedberg (in Stryer, L., Biochemistry, 2nd ed., W. H. Freeman, New York, page 599). A particular class of seed storage proteins has been studied, the 2S seed storage proteins, which are water soluble albumins and thus easily separated from other proteins. Their small size also simplifies their purification. Several 2S storage proteins have been characterised at either the protein or cDNA levels (Crouch et al., 1983; Sharief and Li, 1982; Ampe et al., 1986; Altenbach et al., 1987; Ericson et al., 1986; Scofield and Crouch, 1987; Josefsson et al., 1987; and work described in the present application). 2S albumins are formed in the cell from two sub-units of 6–9 and 3–4 kilodaltons (kd) respectively, which are linked by disulfide bridges.

The work in the references above showed that 2S albumins are synthesized as complex prepropeptide whose organization is shared between the 2S albumins of many different species and are shown diagramatically for three of these species in FIG. 2. Several complete sequences are shown in FIG. 2.

As to FIG. 2 relative to protein sequences of 2S albumins, the following observations are made. For *B. napus, B. excelsia,* and *A. thaliana* both the protein and DNA sequences have been determined. For *R. communis* only the protein sequence is available (*B. napus* from Crouch et al., 1983 and Ericson et al., 1986; *B. excelsia* from Ampe et al., 1986, de Castro et al., 1987 and Altenbach et al., 1987, *R. communis* from Sharief et al., 1982). Boxes indicate homologies, and raised dots the position of the cysteines.

Comparison of the protein sequences at the beginning of the precursor with standard consensus sequences for signal peptides reveals that the precursor has not one but two segments at the amino terminus which are not present in the mature protein, the first of which is a signal sequence (Perlman and Halvorson, 1983) and the second of which has been designated the amino terminal processed fragment (the so called ATPF). Signal sequences serve to ensure the cotranslational transport of the nascent polypeptide across the membrane of the endoplasmic reticulum (Blobel, 1980), and are found in many types of proteins, including all seed storage proteins examined to date (Herman et al., 1986). This is crucial for the appropriate compartmentalization of the protein. The protein is further folded in such a way that correct disulfide bridges are formed. This process is probably localized at the luminal site of the endoplasmatic reticulum membrane, where the enzyme disulfide isomerase is localized (Roden et am., 1982; Bergman and Kuehl, 1979). After translocation across the endoplasmic reticulum membrane it is thought that most storage proteins are transported via said endoplasmic reticulum to the Golgi bodies, and from the latter in small membrane bound vesicles ("dense vesicles") to the protein bodies (Chrispeels, 1983; Craig and Goodchild, 1984; Lord, 1985). That the signal peptide is removed cotranslationally implies that the signals directing the further transport of seed storage proteins to the protein bodies must reside in the remainder of the protein sequence present.

2S albumins contain sequences at the amino end of the precursor other than the signal sequence which are not present in the mature polypeptide. This is not general to all storage proteins. This amino terminal processed fragment is labeled Pro in FIG. 1 and ATPF in FIG. 1a.

In addition, as shown in FIGS. 1 and 1A, several amino acids located between the small and large sub-units in the precursor are removed (labeled link in FIG. 1 and IPF in FIG. 1A, which stands for internal processed fragment). Furthermore, several residues are removed from the carboxyl end of the precursor (labeled Tail in FIG. & and CTPF in FIG. 1A, which stands for carboxyl terminal processed fragment). The cellular location of these latter process steps is uncertain, but is most likely the protein bodies (Chrispeels 1983; Lord, 1985). As a result of these processing steps the small sub-unit (Sml. Sub) and large sub-unit remain. These are linked by disulfide bridges, as discussed below.

When the protein sequences of 2S-albumins of different plants are compared strong structural similarities are observed. This is more particularly illustrated by FIGS. 2 and 2A, which provide the amino acid sequences of the small sub-unit and large sub-unit respectively of representative 2S storage seed albumin proteins of different plants, i.e.:

R. comm.: *Ricinus communis*
A. thali.: *Arabidopsis thaliana*
B. napus: *Brassica napus*
B. excel.: *Bertholletia excelsa* (Brazil nut)

It must be noted that in FIGS. 2 and 2A the amino acid sequences of said sub-units extend on several lines;

the cysteine groups of the amino acid sequences of the examplified storage proteins and identical amino acids in several of said proteins have been brought into vertical alignment; the hyphen signs which appear in some of these sequences represent absent amino acids, in other words direct linkages between the closest amino acids which surrounded them;

the amino acid sequences which in the different proteins are substantially conserved are framed.

It will be observed that all the sequences contain eight cysteine residues (the first and second ones in the small sub-unit, the remainder in the large sub-unit) which can participate in disulfide bridges as diagrammatically shown in FIG. 3, which represents a hypothetical model (for the purpose of the present discussion) rather than a representation of the true structure proven by experimentation of the 2S-albumin of *Arabidopsis thaliana*. Said hypothetical model has been inspired by the disulfide bridge mediated loop-formation of animal albumins, such as serum albumins (Brown, 1976), alpha-fetoprotein (Jagodzinski et al., 1987; Morinaga et al.; 1983) and the vitamine D binding protein where analogous constant C-C doublets and C-X-C triplets were observed (Yang et al., 1985).

Furthermore, the distances between the cysteine residues are substantially conserved within each sub-unit, with the exception of the distance between the fourth and fifth cysteine residues in the large sub-unit. This suggests that these arrangements are structurally important, but that some variation is permissible in the large sub-unit between said fourth and fifth cysteines.

The invention is based on the determination of the regions of the storage protein which can be modified without an attendant alteration of the properties and correct processing of said modified storage protein in plant seeds of transgenic plants. This region (diagrammatically shown in FIG. 3 by an enlarged hatched portion) will in the examples hereafter referred to be termed as the "hypervariable region". FIG. 3 also shows the respective positions of the other parts of the precursor sequence, including the "IPF" section separating the small sub-unit and large sub-unit of the precursor, as well as the number of aminoacids (aa) in substantially conserved portions of the protein sub-units cystein residues. The processing cleavage sites are shown by symbols ▼.

The seeds of many plants contain albumins of approximately the same size as the storage proteins discussed above. However, for ease of language the term "2S albumins" will be used herein to refer to seed proteins whose genes encode a peptide precursor with the general organization shown in FIG. 1 and which are processed to a final form consisting of two subunits linked by disulfide bridges. This is not to be construed as indicating that the process described below is exclusively applicable to such 2S albumins.

The process of the invention for producing a determined polypeptide of interest comprises:

cultivating plants obtained from regenerated plant cells or from seeds of plants obtained from said regenerated plant cells over one or several generations, wherein the genetic patrimony or information of said plant cells, replicable within said plants, includes a nucleic acid sequence, placed under the control of a seed-specific promoter, which can be transcribed into the mRNA encoding at least part of the precursor of a storage protein including the signal peptide of said plant, said nucleic acid being hereafter referred to as the "precursor encoding nucleic acid"

wherein said nucleic acid contains a nucleotide sequence (hereafter termed the "relevant sequence"), which relevant sequence comprises a non essential region modified by a heterologous nucleic acid insert forming an open reading frame in reading phase with the non modified parts surrounding said insert in said relevant sequence.

wherein said insert includes a nucleotide segment encoding said polypeptide of interest.

wherein said heterologous nucleotide segment is linked to the adjacent extremities of the surrounding non modified parts of said relevant sequence by one or several codons whose nucleotides belong either to said insert or to the adjacent extremities or to both, wherein said one or several codons encode one or several aminoacid residues which define selectively clearable border sites surrounding the peptide of interest in the hybrid storage protein or storage protein sub-unit encoded by the modified relevant sequence;

recovering the seeds of the cultivated plants and extracting the hybrid storage proteins contained therein, cleaving out the peptide of interest from said hybrid storage protein at the level of said cleavage sites; and recovering the peptide of interest in a purified form.

It will be appreciated that under the above-mentioned conditions each and every cell of the cultivated plant will include the modified nucleic acid. Yet the above defined recombinant or hybrid sequence will be expressed at high levels only or mostly in the seed forming stage of the cultivated plants and, accordingly, the hybrid protein produced mostly in the seeds.

It will be understood that the "heterologous nucleic acid insert" defined above consists of an insert which contains nucleotide sequences which at least in part, are foreign to the natural nucleic acid encoding the precursor of the storage protein of the seeds or plant cells concerned. Most generally the segment encoding the polypeptide of interest will itself be foreign to the natural nucleic acid encoding the precursor of said storage protein. Nonetheless, the term "heterologous nucleic acid insert" does also extend to an insert containing a segment as above-defined normally present in the genetic patrimony or information of said seeds or plant cells, the "heterologous" character of said insert then adressing to the one or several codons which surround it, on both sides thereof and which link said segment to the non-modified parts of the nucleic acid encoding said precursor. Under such last mentioned circumstances the invention thus provides for a method which enables the production and easy separation and recovery of a valuable protein normally produced in the plant itself, either at the seed forming stage or at any other stage of the development of the plant, and either in the protein bodies of the seeds or any other location of said plant cells.

The "polypeptide of interest" will usually consist of a single polypeptide, or protein which, when cleaved out from the hybrid storage proteins in the final stages of the process of this invention, will retain or resume at least those of the biological properties sought to be possessed by that single polypeptide or protein of interest. By way of non limitative examples of properties sought to be retained by the polypeptide of interest, one may cite, e.g. enzymatic or therapeutic activities, the capability of being recognized by determined antibodies, immunogenic properties, for instance the capability of eliciting in a living host antibodies which are able to neutralize such peptide of interest or a pathogenic agent containing antigens including the same or an analogous sequence of aminoacids as said "polypeptide of interest".

However the "polypeptide of interest" may also comprise repeats of a unit, particularly of an individual peptide or polypeptide having any desired biological activity, said units being joined with one another over or through clearable sites permitting the separations of the biologically repeats or units from one another. Though not decisive, such cleavable sites are advantageously identical to or sensitive to the same cleaving means, e.g., a determined restriction enzyme as the above-defined "border cleavage sites" which enable the overall "polypeptide of interest" to be cleaved out from the hybrid storage protein. As a matter of fact, separation of the active units from one another may then be achieved simultaneously with the above mentioned "cleaving out" operations. Yet the different units or repeats may be joined through different cleavage sites, whereby the separation of said units from one another may be undertaken subsequent to the "cleaving out" operations of said "polypeptide of interest" from the hybrid storage protein.

The number of repetitive units in the polypeptide of interest will of course be dependent upon the maximum length of polypeptide of interest which may be incorporated in the storage protein concerned under the conditions defined herein.

In the preceding definition of the process according to the invention the so-called "non-essential region" of the relevant sequence of said nucleic acid encoding the precursor, consists of a region whose nucleotide sequence can be modified either by insertion into it of the above Refined insert or by replacement of at least part of-said non-essential region by said insert, yet without modifying the resulting overall configuration of said hybrid storage protein as compared to that of the non-modified natural storage protein as well as the transport of the correspondingly modified nascent hybrid storage protein into the above said protein bodies.

In the present invention the precursor-coding nucleic acid referred to above may of course originate from the same plant species as that which is cultivated for the purpose of the invention. It may however originate from another plant species, in line with the teachings of Beachey et al., 1985 and Okamuro et al., 1987 already of record.

In a similar manner the seed-specific promoter may originate from the same plant species or from another, subject in the last instance to the capability of the host plant's polymerases to recognize it.

Any method for the location of a non-essential region in a storage protein can be used. Once this region is defined at the protein sequence level, the corresponding region of the precursor encoding nucleic acid can be altered. For instance, non-essential regions can be located using methods based on the establishment of secondary and tertiary protein structures by molecular modeling. Such models will allow the identification of regions of the protein critical for its configuration or interaction in higher order aggregations. In the absence of such technology, the peptide sequences of analogous proteins from various plant species can be compared. Those subsequences which said peptide sequences have in common (and which prima-facie will support the presumption that they cannot be modified without affecting the structure, processing, intracellular passage, or packaging of the peptide in a deleterious way) can be distinguished from those which are so different from one another as to support the assumption that they may consist of "non-essential regions" which may then be deemed to be eligible for modification by a determined heterologous insert.

Such an approach is possible when the protein or nucleic acid sequences of several similar storage proteins originating from different plants have been determined (as is the case for the 2S albumins). A suitable method then comprises identifying said nucleic acid regions which encode peptide regions undergoing variability in either amino acid sequence or length or both, as compared with the regions which, on the contrary, do exhibit substantial conservation of amino acid sequence between said several plant species. Where the storage proteins under study contain cysteine residues and where further it is thought or known through experimental data that said cysteines participate in disulfide bridges likely to play an important part in the establishment of the structure and conformation of the storage proteins concerned, the method should be extended to take this into account. In this case, the cysteine residues should not be among those residues altered by the modification of the storage protein, and where sequence comparison of protein sequences of analogous proteins shows that the distance (in amino acid residues) between cysteines is conserved, this distance should not be altered by any subsequent modification. The said non-essential regions in the protein sequence so selected can then be modified by insertion into the corresponding region of the precursor-coding nucleic acid, the nucleic acid segments encoding the desired peptide product and, after said modification has been achieved, the expression of the modified storage protein in the seeds recoverable at the seed-forming stage of plant development can be assayed.

Another method which is available within the skills of a person skilled in the art to determine if a region thought to be amenable to modification consists in to make such a modification and to express the chimeric gene in any one of several expression systems which, while not appropriate to produce economically interesting amounts of the chimeric protein, will, if the chimeric protein is stable, produce small quantities for analysis. In such experiments, the unmodified protein should also be brought to expression as a control. Such systems include, but are not limited to, the Xenopus leaves oocytes (Bassèner et al., 1983), transient expression in plant chloroplats (Fromm et al., 1985), yeast (Hollenberg et al, 1985), plant callus and the Acetabularia system. The latter has been used by Brown et al (1986) for the functional analysis of zein genes and their modification by sequences encoding lysine.

The choice of precursor-coding nucleic acids encoding the precursors of 2S-proteins, particular water-soluble 2S-proteins for the production of the modified nucleic acids to be transferred into the plant cells to be modified is particularly attractive for the reasons already of record.

As can be seen on FIGS. 2 and 2A, the regions which are intercalated between the first and second cysteines in the small sub-unit of the protein, between the fifth and sixth cysteines, on the one hand, and between the seventh and eighth cysteines in the large sub-unit of the protein show a substantial degree of conservation or similarity. It would thus seem that these regions are in some way essential for the proper folding and/or stability of the the protein when synthesized in the plant seeds.

To the contrary other regions such as at the end of the small subunit, at the beginning or end of the large sub-unit, show differences of such a magnitude that they can be held as presumably having no substantial impact on the final properties of the protein. A region which does not seem essential, consists of the middle position of the region located in the large sub-unit, between the fourth and the fifth cysteine of the large subunit. As visible on the drawing (FIG. 2) *B. napus* comprises a CKQQM sequence between the Q amino acid which precedes it and the V amino acid which follows it, whereas at the same level *A. thali* has no similar sequence at all between the same neighbouring aminoacids and *B. excel* and *R. comm* comprise shorter CEQ and CQ peptides respectively. Thus it appears that in addition to the absence of similarity at the level of the amino acid residues, there appears a difference in length which makes that region eligible for substitutions in the longest 2S albumins and for addition of amino acids in the shortest 2S albumins or for elongation of both.

The same observations should extend at the level of approximately of the end of the first third part of the same region between said fourth and fifth cysteine of the large subunit of a 2S albumins: see sequence of *R. Communis* which is much shorter in that region than the corresponding regions of the other exemplified 2S-proteins.

Experimentation, which is within the skills of the person skilled in the art, will show how much of the other amino acids which neighbour the above said fourth and fifth cysteine of the large subunit of a 2S albumins could further be substituted without causing disturbance of the stability and correct processing of the hybrid protein. For instance experimentation will show how much of the other amino acids which neighbour the abovesaid GKQQM sequence of *B. napus* upstream and downstream thereof, could further be substituted without causing the hybrid protein likely to be formed to be further substituted without loss by the hybrid protein of the essential properties of the normal *B. napus* 2S albummin. The modifications contemplated should preferably not affect the three, preferably six aminoacids adjacent to the relevant cysteins, e.g. the fourth and fifth cysteins of the large subunit.

It is of course realized that caution must be exercized against hypotheses based on arbitrary choices as concerns the bringing into line of similar parts of proteins which elsewhere exhibit substantial differences. Nevertheless such comparisons have proven in other domains of genetics to provide the man skilled in the art with appropriate guidance to reasonably infer from local structural differences, on the one hand, and from local similarities, on the other hand, in similar proteins of different sources, which parts of such proteins can be modified and which parts cannot, when it is sought to preserve some basic properties of the non modified protein in the same protein yet locally modified by a foreign or heterologous sequence.

Thus it is prima facie deemed that, subject to verification, any part of a protein or of a subunit thereof may be deemed as eligible for substitution by a peptide having a different amino acid sequence.

The choice of the adequate non-essential regions to be used in the process of the invention will also depend on the length of the peptide of interest. Basically the method of the invention thus allows the production of biologically active polypeptides in the range of 3–100 aminoacids in length. This biologically active polypeptide may have a vegetal origin or may be a non plant variety specific polypeptide having a bacterial origin or a fungal origin or an algal origin or an invertebral origin or a vertebral origin such as a mamalian origin.

The sequence (insert) to be inserted in the appropriate regions of the relevant sequence storage protein, e.g., a 2S protein, or a sub-unit thereof, does not, normally, include only the segment coding this polypeptide of interest, but also the codons (or parts thereof when the contiguous nucleotides of the nonmodified parts of the relevant nucleotide sequences of the precursor-coding nucleic acid happen to adequately supplement the codons) encoding amino acids or peptides which form the above said amino acid junctions cleavable, e.g., by protease or chemical treatment, so that the peptide of interest can later be recovered from the purified 2S protein. The junction-sequences can be made either as a double stranded oligomer or, if part of a gene is available, as a restriction fragment, but in the latter case the cleavage sites, e.g. protease cleavage sites must generally be added.

The choice of sequences bordering the peptide of interest depends on several factors which essentially depend on the techniques to be used for purifying that peptide in the final stages of the process. The peptide of interest can be flanked by any proteolytic cleavage sites, provided that the sequence of the peptide of interest does not contain internal similar cleavage sites. Finally, the proteases and/or chemical cleavage reagents should be specific and readily available. They should correctly cleave the inserted sequence at both the amino and carboxyl termini. For example, the protease trypsin cleaves after Arginine or Lysine residues assuming they are not followed by a Proline. Thus, if neither Arginine of Lysine residues are present in the peptide of interest (or are followed by a Proline) the sequence can be flanked by codons encoding one of those two amino acids. The peptide can then be cleaved out of the hybrid protein using trypsin, followed by treatment with the exoprotease carboxypeptidase B to remove the extra carboxyl terminus Arg or Lys. Similarly, the protease endo-Lys-C (Jekel et al., 1983) cleaves after Lysine residues, so that a peptide could be inserted between two such residues, cleaved from the 2S albumin using this protease, and the extra Lysine again removed using carboxypeptidase B. Such a strategy is particularly useful when the 2S albumin is used, as the latter is poor in Lysine, so that only a few fragments are generated, resulting in easy purification. Cyanogen bromide serves as an example of a chemical cleavage reagent. Treatment with this reagent cleaves on the carboxyl side of Methionine. Thus, for each case a separate strategy must be developed, but the wide variety of protease cleavage techniques available allows the same basic principles to be followed. As often as possible, strategies should use economical commercially available proteases or reagents, and purification steps limited in number. For reviews of various enzymatic and chemical cleavage techniques see volumes 19 (1970 and 47 (1977) of *Methods in Enzymology*.

Finally, some peptides are found in nature with C-terminal alpha-amide structures (alpha-melanotropin, calcitonin, and others; see Hunt and Dayhoff, 1976). This post-translational modification has been shown to be of essential importance for the biological activity of the peptide. Such a C-terminally amidated peptide can be obtained by transformation of a C-terminal glycine residue into an amide group (Seiringer et al., 1985). Therefore such peptides can be generated from the 2S hybrid protein by adding a C-terminal glycine residue to the peptide which, after purification, is transformed into an amide group.

When the complete protein sequence of the region to be inserted into the storage protein has been determined, including both the polypeptide of interest and the amino acids of peptides which form the above described cleavable junctions, the nucleotide sequence to encode said protein sequence must be determined. It will be recognized that while perhaps not absolutely necessary the codon usage of the encoding nucleic acid should where possible be similar to that of the gene being modified. The person skilled in the art will have access to appropriate computer analysis tools to determine said codon usage.

Any appropriate genetic engineering technique may be used for substituting the insert for part of the selected precursor-coding nucleic acid, or for inserting it in the appropriate region of said precursor-coding nucleic acid. The general in vitro recombination techniques followed by cloning in bacteria can be used for making the chimeric genes. Site-directed mutagenesis can be used for the same purposes as further exemplified hereafter. DNA recombinants, e.g. plasmids suitable for the transformation of plant cells can also be produced according to techniques disclosed in current technical literature. The same applies finally to the production of transformed plant cells in which the hybrid storage protein encoded by the relevant parts of the selected precursor-coding nucleic acid can be expressed. By way of example, reference can be made to the published European applications nr. 116 718 or to International application WO 84/02913 (incorporated herein by reference) and, which disclose appropriate techniques to that effect.

The preceding discussion has been based more specifically, by way of example, on the modification of storage 2S albumin. It will be understood that the process of this invention can also be carried-out upon using any other type of 2S-storage protein or any other storage protein having another sedimentation coefficient, (e.g., a 7S-, 11S- and -12S storage protein) or the same, provided that the DNA sequences which encode it in the plant from which it can be isolated, have been or can be identified and that non-essential or "hypervariable subsequences" therein have been or can be detected.

Examples (by way of illutration only) of such other storage proteins consist (see also Higgins (1984) for review):

of other albumins, which are water soluble storage proteins, which may be either 12S like such as the lectins isolatable from pea and various beans, or either 2S like such as the 2S albumins already or record or other 2S albumins isolatable from pea, radish and sunflower;

of globulins, which are storage proteins soluble in salt solutions, which may be either 7-8S like such as the phaseolins isolatable from Phaseolus, the vicilins isolatable from pea, the conglycinins isolatable from soybean, the oat-vicilins isolatable from oat, or either 11-14S like, such as the legumins isolatable from pea, the glycinins isolatable from soy-bean, the helianthins isolatable from sunflower or other 11-14S globulins isolatable from beans, Arabidopsis, and probably from wheat;

of prolamins, which are alcohol soluble storage proteins, such as the reins isolatable from corn, the hordiens isolatable from barley, the gliadins isolatable from wheat and the kafirins isolatable from sorghum;

of glutelins, which are storage proteins soluble under low pH conditions and isolatable from wheat.

Some of these storage proteins-merely cited by way of examples—are poor in cysteines. Yet the different proteins of a same group do show variable regions on the one hand, better conserved regions on the other hand.

Needless to say that these storage proteins could be used as suitable vectors for the production of the above said hybrid proteins and their respective purifications from the seed proteins, upon relying on their respective specific solubility characteristics in the corresponding solvents.

The procedures which have been disclosed generally hereabove apply to the adequate modification of the non-essential regions of any of said other storage proteins by an heterologous insert containing a DNA sequence encoding the peptide of interest and then to the transformation of the relevant plants with the chimeric gene obtained for the production of a hybrid protein containing the sequence of the peptide of interest in the seeds of the relevant plant, and they apply to the recovery of the peptide of interest from said plants. Needless to say that the person skilled in the art will in all instances be able of selecting which of the existing techniques would at best fulfill its needs at the level of each step of the production of such modified plants, to achieve the best production yields of said peptide of interest.

The preceding discussion has been based more specifically, by way of example, on the modification of the hypervariable region of a determined storage protein by an insert encoding a biologically active peptide. It will be understood that the person skilled in art may choose as insert a sequence which encode repeats of said biologically active peptide, wherein every sequence encoding said biologically active peptide is separated from the other by border sequences encoding selective cleavage sites which allow their separation during purification.

For instance the following process can be used in order to exploit the capacity of a storage protein, to be used as a suitable vector for the production in seeds of a determined polypeptide of interest or repeats thereof, when the corresponding precursor-coding nucleic acid has been sequenced. Such process then comprises:

1) locating and selecting one of said relevant sequences of the precursor-coding nucleic acid which comprises a non-essential region encoding a peptide sequence which can be modified by substituting an insert for part of it or by inserting of said insert into it, which modification is compatible with the conservation of the configuration of the storage protein;

2) inserting a nucleic acid insert in the selected region of said precursor nucleic acid in appropriate reading frame relationship with the non-modified parts of said relevant sequence, which insert includes a determined segment encoding the polypeptide of interest or repeats thereof and, downstream and upstream of said determined segment, suitable nucleotides, codons or triplets of nucleotides which, after said insertion into the precursor-coding nucleic acid has been achieved, participate in the formation of codons encoding amino acid junctions linking the polypeptide of interest or its individual repeats to each other and into the relevant parts of the storage protein or sub-unit thereof, whereby said amino-acid junctions define border sites surrounding the peptide of interest and which can themselves be selectively cleaved, e.g., by specific peptidases;

3) inserting the modified precursor-coding nucleic acid obtained in a plasmid suitable for the transformation of plant cells which can be regenerated into full seed-forming plants, wherein said insertion is brought under the control of regulation elements, particularly a seed specific promoter capable of providing for the expression in the seeds of said plants of the open-reading frames associated therewith;

4) transforming a culture of such plant cells with such modified plasmid;

5) assaying the expression of the chimeric storage protein having inserted into its hypervariable region the determined sequence of the segment encoding the polypeptide of interest or the repeats thereof and, when achieved 6) regenerating said plants from the transformed plant cells obtained and growing said plants up to the seed forming stage;

7) recovering the seeds and extracting the storage proteins contained therein;

8) cleaving said storage proteins e.g., with said specific peptidases, isolating and recovering the peptide of interest.

In the case of storage 2S-proteins which contain a substantial number of cysteine residues, which storage proteins are preferred at the present time, and further when the precursor-coding nucleic acids of several similar proteins performing the same functions in different plants, yet originating from said different plants respectively, are available and have been (or can be) sequenced, step 1) of the general process defined above may be carried out as follows (it being understood that the sequence of steps recited hereafter is optional and can be replaced by any other procedure aiming at achieving the same result). Said "step 1" then comprises:

a) selecting several of said plant storage proteins, available and identifiable in several seed forming plant species respectively;

b) locating the precursor-coding nucleic acid sequence which in each of said plant species encodes the precursor of said plant storage protein and determining in said precursor-coding nucleic acid a relevant nucleotide sequence consisting of a sequence encoding the mature storage protein or an appropriate sub-sequence encoding for a sub-unit of said mature storage protein;

c) determining the relative positions of the codons which encode the successive cysteine residues in said mature protein or protein sub-units and identifying the corresponding successive nucleic acid regions located upstream of, between, and downstream of said codons within said sub-sequences of the precursor-coding nucleic acid and identifying in said successive regions those parts which undergo variability in either amino acid sequence or length or both from one plant species to another as compared with those other regions which do exhibit substantial conservation of amino acid sequence in said several plant species, one of said nucleotide regions being then selected for the insertion therein of the nucleic acid insert including the segment encoding the peptide of interest or repeats thereof, e.g. as disclosed under 2) hereabove.

Hence last mentioned enbodiment of the invention provides that in having the heterologous polypeptide of interest or repeats thereof made as part of a hybrid protein in a plant, it will pass the plant protein disulfide isomerase during membrane translocation, thus increasing the chances that the correct disulfide bridges be formed in the hybrid precursor as in its normal precursor situation, on the one hand, and that the polypeptide of interest or repeats thereof be protected against the different drawbacks which have been recalled above as concerns the standard genetic engineering techniques for producing foreign peptides in host microorganisms, on the other hand.

The invention further refers to the recombinant nucleic acids themselves for use in the process of the invention; particularly to the recombinant precursor encoding nucleic acid defined in the frame of said process;

recombinant nucleic acids containing said modified precursor -coding nucleic acid under the control of a seed-specific promoter, whether the latter originates from the same DNA as that of said precursor-coding nucleic acid of from a DNA of another plant, vectors, more particularly plant plasmids e.g., Ti-derived plasmids modified by any of the preceding recombinant nucleic acids for use in the transformation of the above plant cells.

The chimeric gene should be provided with a suitable signal sequence if it does not posses one (which all storage proteins do).

The invention also relates to the regenerable source of a polypeptide of interest, which is formed of either plant cells of a seed-forming-plant, which plant cells are capable of being regenerated into the full plant or seeds of said seed-forming plants wherein said plants or seeds have been obtained as a result of one or several generations of the plants resulting from the regeneration of said plant cells, wherein further the DNA supporting the genetic information of said plant cells or seeds comprises a nucleic acid or part thereof, including the sequences encoding the signal peptide, which can be transcribed in the mRNA corresponding to the precursor of a storage protein of said plant, placed under the control of a seed specific promoter, and wherein said nucleic acid sequence contains a relevant modified sequence encoding the mature storage protein or one of the several sub-sequences encoding for the corresponding one or several sub-units of said mature storage protein, wherein further the modification of said relevant sequence takes place in one of its non essential regions and consists of a heterologous nucleic acid insert forming an open-reading frame in reading phase with non modified parts which surround said insert in the relevant sequence, wherein said insert includes a nucleotide segment encoding said polypeptide of interest, wherein said heterologous nucleotide segment is linked to the adjacent extremities of the surrounding non modified parts of said relevant sequence by one or several codons whose nucleotides belong either to said insert or or to the adjacent extremities or to both, wherein said one or several codons encode one or several amino acid residues which define selectively cleavable border sites surrounding the peptide of interest in the hybrid storage protein or storage protein sub-unit encoded by the modified relevant sequence.

It is to be considered that although the invention should not be deemed as being limited thereto, the nucleic inserts encoding the polypeptide of interests or repeats thereof will in most instances be man-made synthetic oligonucleotides or oligonucleotides derived from viral or bacterial genes or of from cDNAs derived of viral or bacterial RNAs, or further from non-plant eucaryotic genes, all of which shall normally escape any possibility of being inserted at the appropriate places of the plant cells or seeds of this invention through biological processes, whatever the nature thereof. In other words, these inserts are usually "non plant variety specific", specially in that they can be inserted in different kinds of plants which are genetically totally unrelated and thus incapable of exchanging any genetic material by standard biological processes, including natural hybridization processes.

Thus the invention further relates to the seed forming plants themselves which have been obtained from said transformed plant cells or seeds, which plants are characterized in that they carry said hybrid precursor-coding nucleic acids associated with a seed promoter in their cells, said inserts however being expressed and the corresponding hybrid protein produced mostly in the seeds of said plants.

There follows an outline of a preferred method which can be used for the modification of 2S seed storage protein genes, their expression in transgenic plants, the purification of the 2S storage protein, and the recovery of the biologically active peptide of interest. The outline of the method given here is followed by a specific example. It will be understood from the person skilled in the art that the method can be suitably adapted for the modification of other 2S seed storage protein genes.

1. Replacement or supplementation of the hypervariable region of the 2S storage protein gene by the sequence of interest.

Either the cDNA or the genomic clone of the 2S albumin can be used. Comparison of the sequences of the hypervariable regions of the genes in FIG. 2 shows that they vary in length. Therefore if the sequence of interest is short and a 2S albumin with a relatively short hypervariable region is used, the sequence of interest can be inserted. Otherwise part of the hypervariable region is removed, to be replaced by the insert containing the segment or sequence of interest and, if appropriate, the border codons. The resulting hybrid storage protein may be longer or shorter than the non-modified natural storage protein which has been modified. In either case two standard techniques can be applied; convenient restriction sites can be exploited, or mutagenesis vectors (e.g., Stanssens et al. 1987) can be used. In both cases, care must be taken to maintain the reading frame of the message.

2. The altered 2S albumin coding region is placed under the control of a seed specific gene promoter.

A seed specific promoter is used in order to ensure subsequent expression in the seeds only. This facilitates recovery of the desired product and avoids possible stresses on other parts of the plant. In principle the promoter of the modified 2S albumin can be used. But this is not necessary. Any other promoter serving the same purpose can be used. The promoter may be chosen according to its level of efficiency in the plant. species to be transformed. In the examples below a lectin promotor from soybean and a 2S albumin promoter from Arabidopsis are used. If a chimeric gene is so constructed, a signal peptide encoding region must also be included, either from the modified gene or from the gene whose promotor is being used. The actual construction of the chimeric gene is done using standard molecular biological techniques (see example).

3. The chimeric gene construction is transferred into the appropriate host plant.

When the chimeric or modified gene construction is complete it is transferred in its entirety to a plant transformation vector. A wide variety of these, based on disarmed (non-oncogenic) Ti-plasmids derived from *Agrobacterium tumefaciens*, are available, both of the binary and cointegration forms (De Blaere et al., 1987). A vector including a selectable marker for transformation, usually antibiotic resistance, should be chosen. Similarly, the methods of plant transformation are also numerous, and are fitted to the individual plant. Most are based on either protoplast transformation (Matron et al., 1979) or transformation of a small piece of tissue from the adult plant (Horsch et al., 1985). In the example below, the vector is a binary disarmed Ti-plasmid vector, the marker is kanamycin resistance, and the leaf disc method of transformation is used.

Calli from the transformation procedure are selected on the basis of the selectable marker and regenerated to adult plants by appropriate hormone induction. This again varies with the plant species being used. Regenerated plants are then used to set up a stable line from which seeds can be harvested.

4. Recovery of biologically active polypeptides.

The purification of 2S plant albumins is well established (Youle and Huang, 1981; Ampe et al., 1986). It is a major protein in mature seeds and highly soluble in aqueous buffers. A typical purification of 2S-storage proteins involves the following steps: 1, homogenization of seed in dry ice and extraction with hexane; 2, extraction with high salt buffer and dialysis against distilled water, precipitating the contaminating globulins; 3, further purification of the water soluble fraction by gel-filtration chromatography, which separates the smaller 2S-storage proteins from the larger contaminants; and 4, final purification by ion-exchange chromatography. The exact methods used are not critical to the technique described here, and a wide range of classical techniques, including gel filtration, ion exchange and reversed phase chromatography, and affinity or immunoaffinity chromatography may be applied both to purify the chimeric 2S albumin and, after it is cleaved from the albumin, the biologically active peptide. The exact techniques used for this cleavage will be determined by the strategy decided upon at the time of the design of the flanking sequences (see above). As 2S albumins are somewhat resistant to proteases, denaturation steps should often be included before protease treatment (see example).

5. Assays for biologically active peptides.

Assays for the recovered product are clearly dependent on the product itself. For initial screening of plants, immunological assays can be used to detect the presence of the peptide of interest. Antibodies against the desired product will often function even while it is still part of the hybrid 2S protein. If not, it must be partially or completely liberated from the hybrid, after which peptide mixtures can be used. The screening with antibodies can be done either by classical ELISA techniques (Engvall and Pesce, 1978) or be carried out on nitrocellulose blots of proteins previously separated by polyacrylamide gel electrophoresis (Western blotting, Towbin et al., 1979). The purified peptide can be further analysed and its identity confirmed by amino acid composition and sequence analysis.

Bioassays for biological activity will of course depend upon the nature and function of the final peptide of interest.

It has to be understood that the present invention is also applicable for the production of labeled proteins which may be biologically active using the plant seed storage proteins as suitable vectors. In this case, plant regeneration of the obtained transformants, as described under point 3 hereabove, has to occur under conditions by which labeled carbon sources ($^{13}C$) and/or nitrogen sources ($^{15}N$) and/or hydrogen sources ($^{3}H$) and/or sulphur sources ($^{35}S$) and/or phosphor sources ($^{32}p$) has to be provided to the transformed growing plants (Kollman et al., 1979; Jung and Jettner, 1972; De Wit et al., 1978).

Further characteristics of the invention will appear in the course of the non-limiting disclosure of specific examples, particularly on the basis of the drawings in which:

FIG. 1 compares the general organization of two 2S albumin precursors.

FIG. 1A compares the general organization of three 2S albumin precursors.

FIG. 2 compares the amino acid sequences of small and large subunits of four 2S albumins.

FIGS. 2A and 2B and 2C compare the amino acid sequences of parts of six 2S albumins.

FIG. 4 represents part of the sequence of the Brazil nut 2S-albumin obtained from the pBN2S1 plasmid obtained as indicated hereafter and related elements.

FIG. 5 represents restriction sites used in the constructions shown in other drawings.

Figure 3:
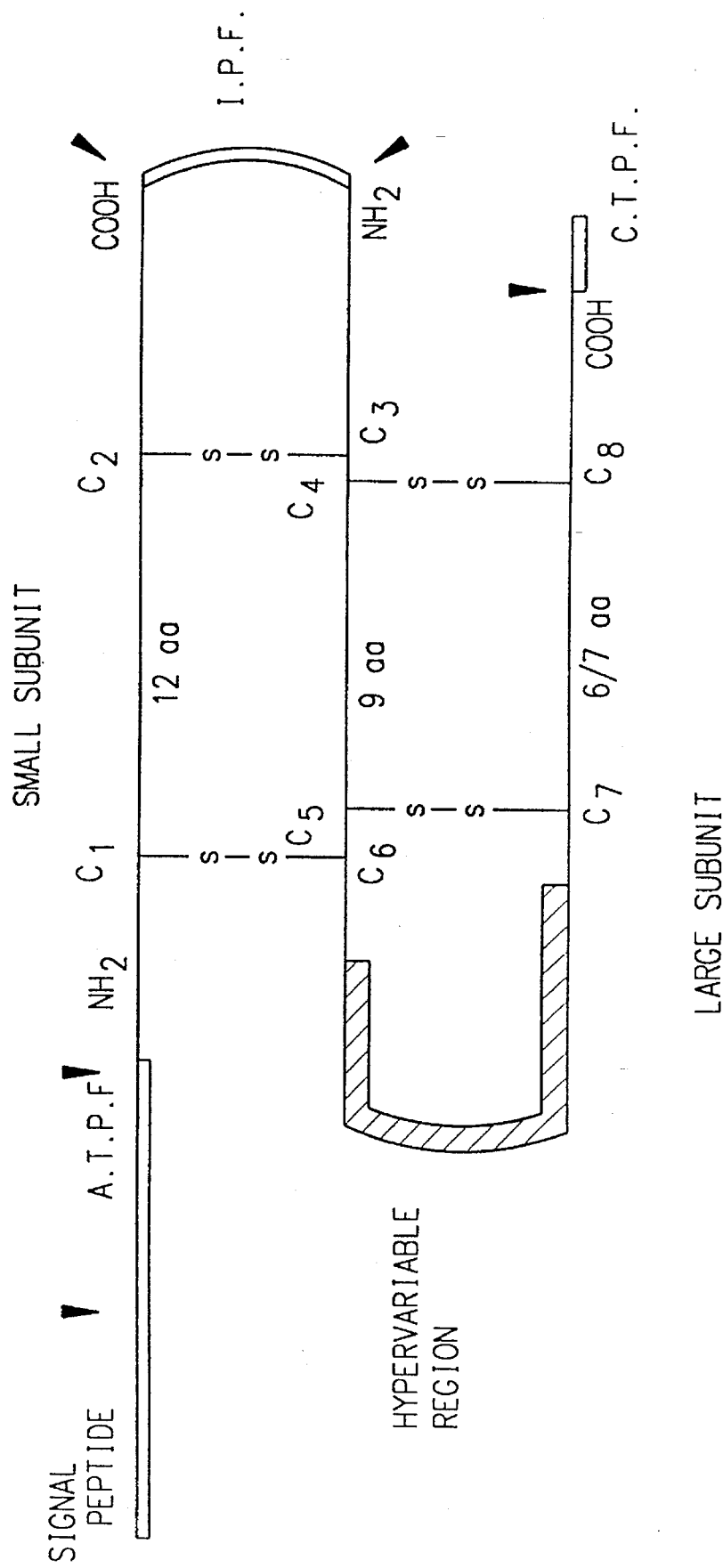
FIG. 3 represents a hypothetical model of the structure of the 2S albumin of A. thaliana.
Figure 6:
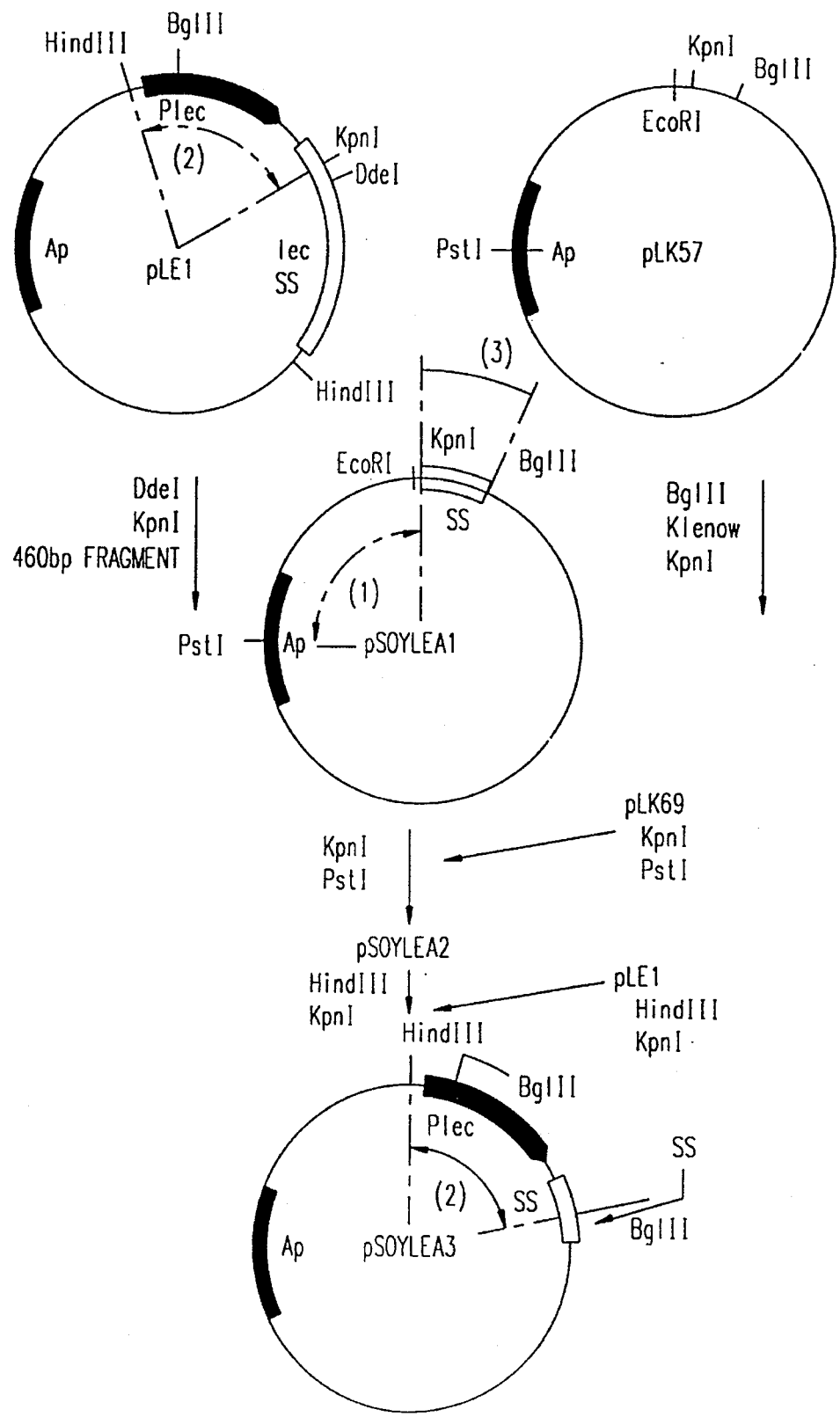

FIG. 6 diagrammatically shows the construction of plasmid pSOYLEA3.

Figure 7:
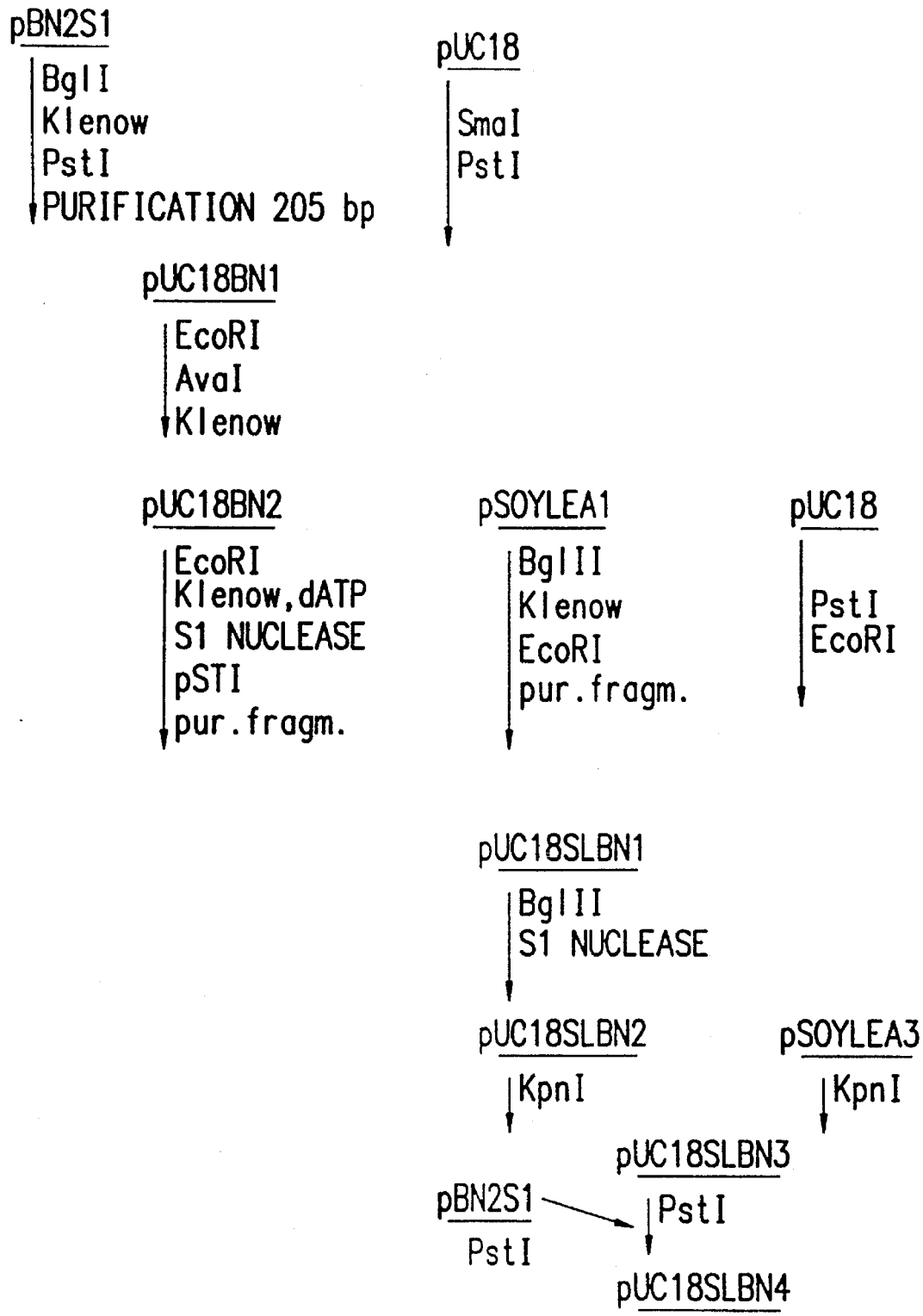

FIG. 7 diagrammatically shows the construction of plasmid pUC18SLBN4 in Example 1.

Figure 8:
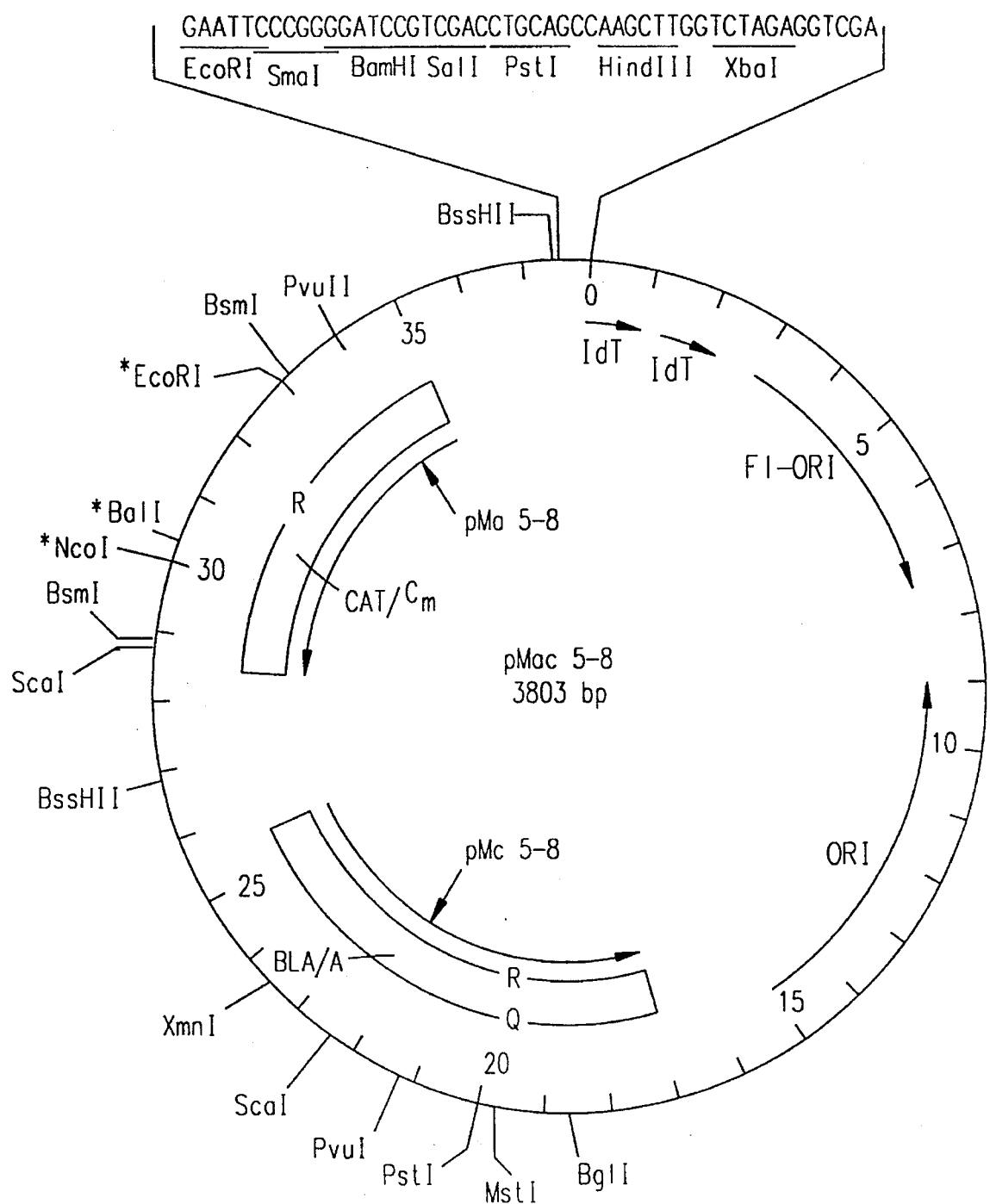

FIG. 8 shows the restriction sites and genetic map of a plasmid suitable for the performance of site-directed mutagenesis.

Figure 9:
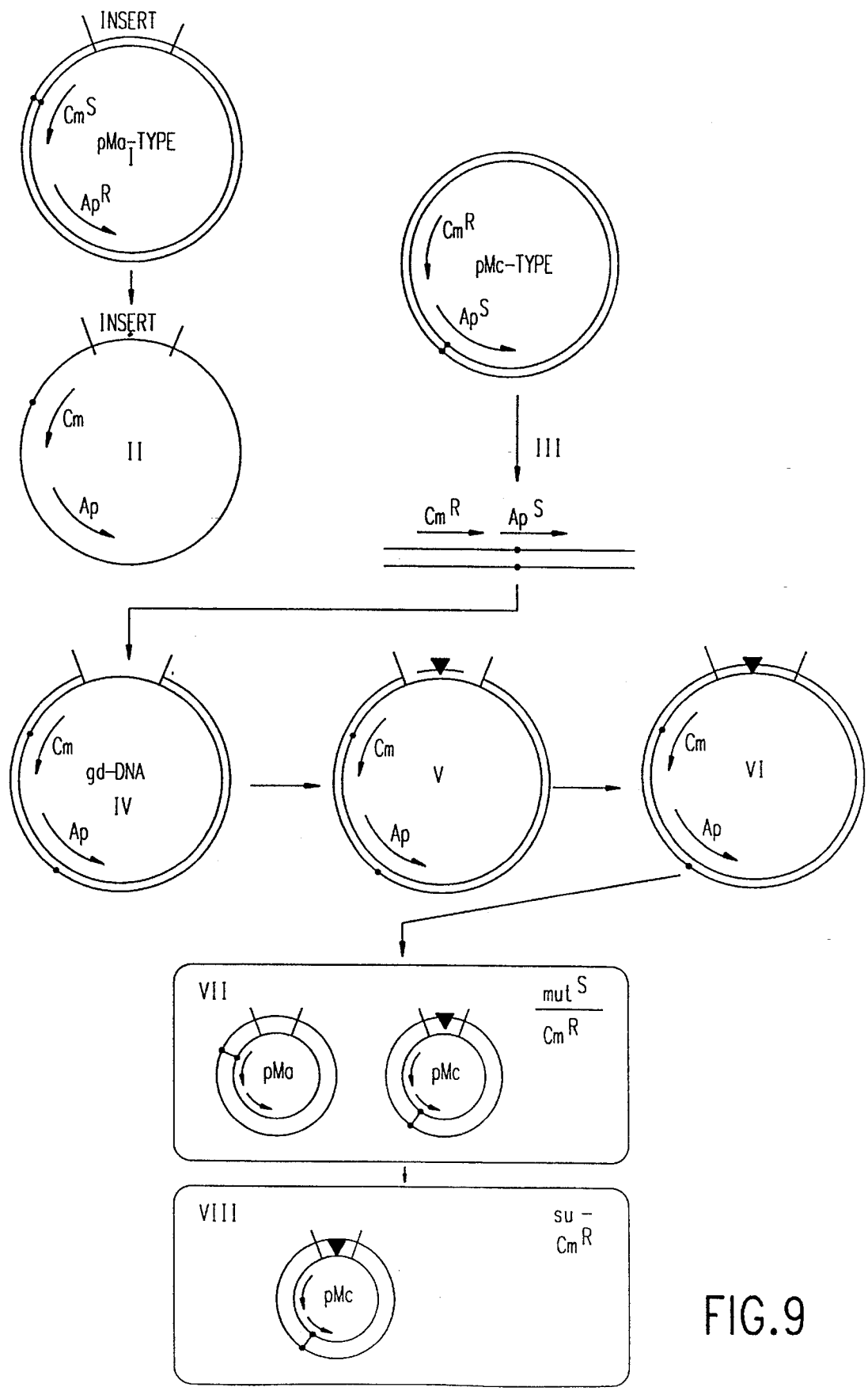

FIG. 9 shows diagrammatically the different steps of the site-directed mutagenesis procedure of Stanssens et al (1987) as generally applicable to the modification of nucleic acid at appropriate places.

Figure 10:
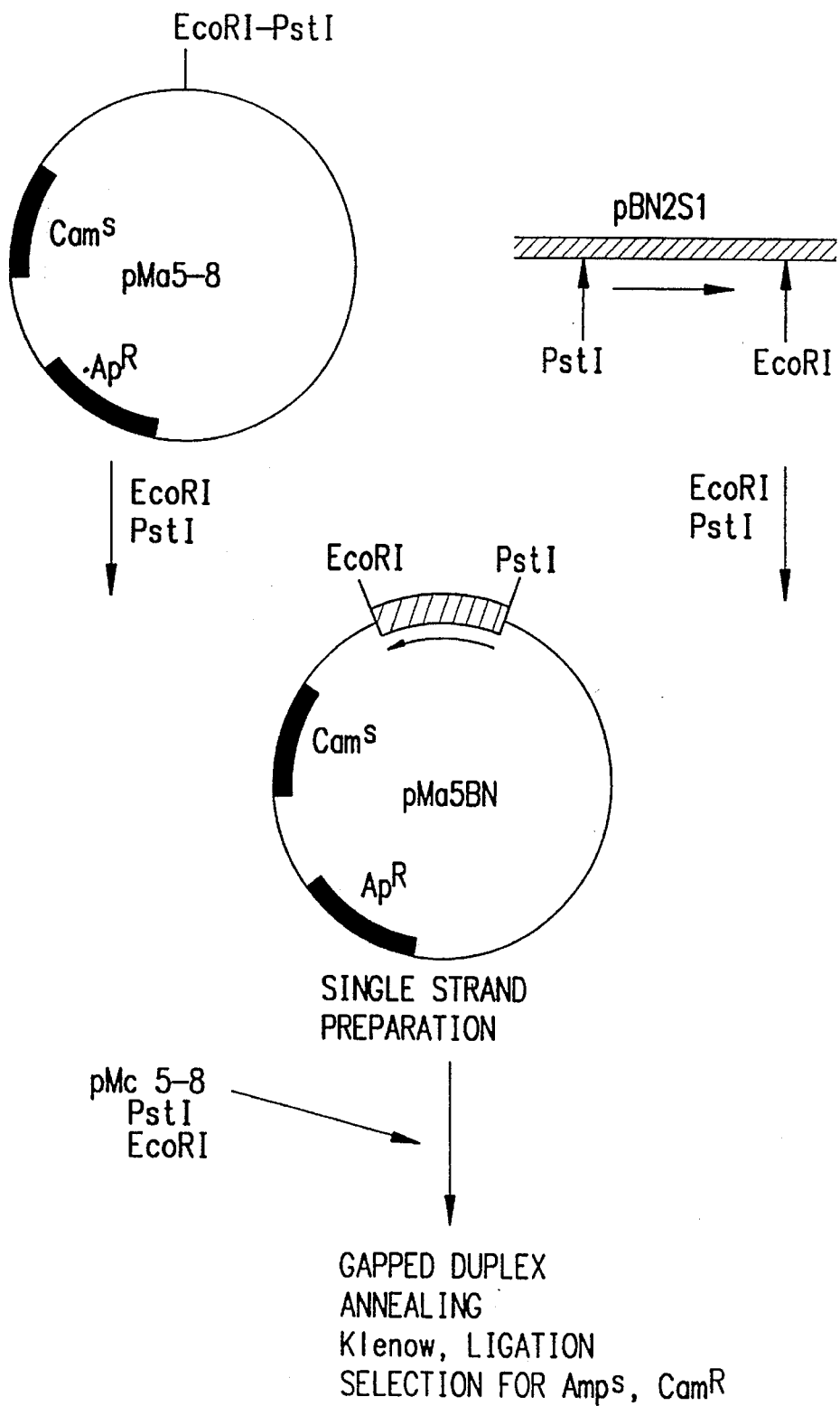

FIG. 10 shows diagrammatically the fusion of the site-directed mutagenesis vector pMa5–8 with the PstI fragment of plasmid pBN2S1 of Example 1 to produce plasmid pMa5BN.

Figure 11:
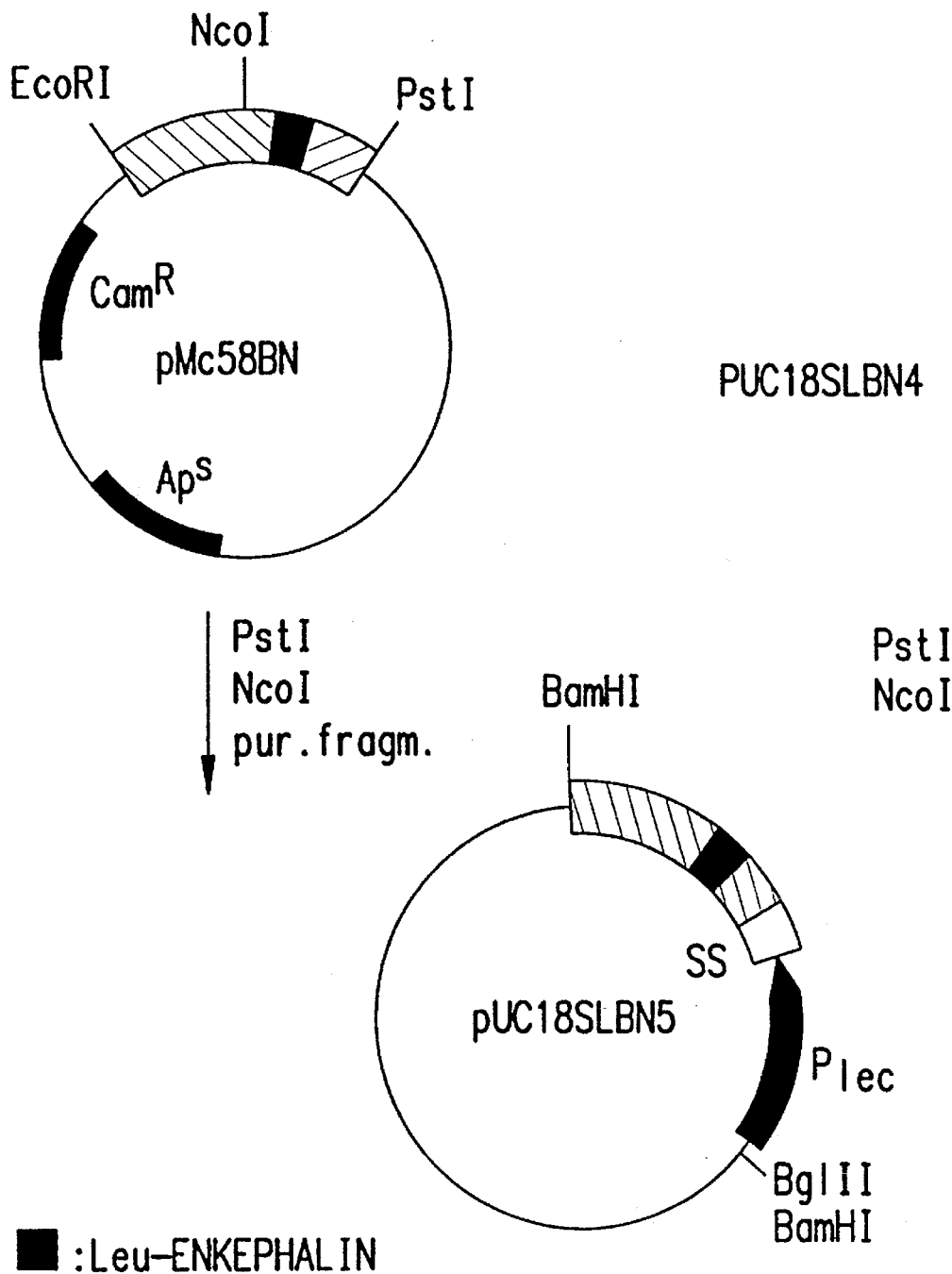

FIG. 11 shows diagrammatically the fusion of plasmid pMc5BN and plasmid pUC18SLBN4 of Example 1 to produce plasmid pUC 18SLBN5.

FIG. 12 shows diagrammatically the fusion of plasmid pUC18SLBN5 with binary vector pGSC1702 of Example 1 to produce pGSBNE1.

FIG. 13 represents the sequence of 1 kb fragment containing the *Arabidopsis thaliana* 2S albumin gene and shows related elements.

FIG. 14 provides the protein sequence of the large subunit of the above Arabidopsis 2S protein together with related oligonucleotide sequences.

Figure 15:
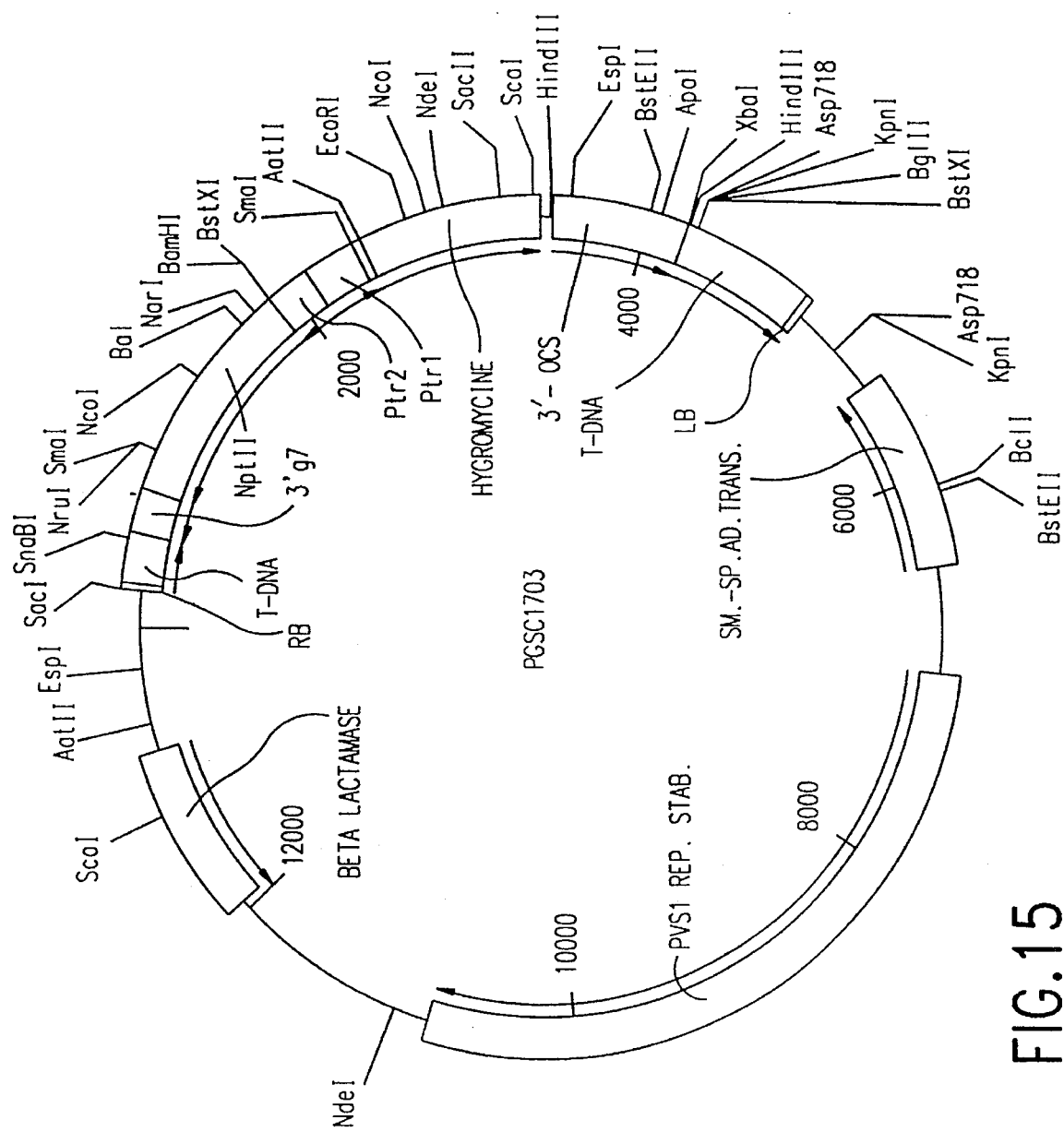

FIG. 15 represents the restriction map of pGSC1703.

Figure 16:
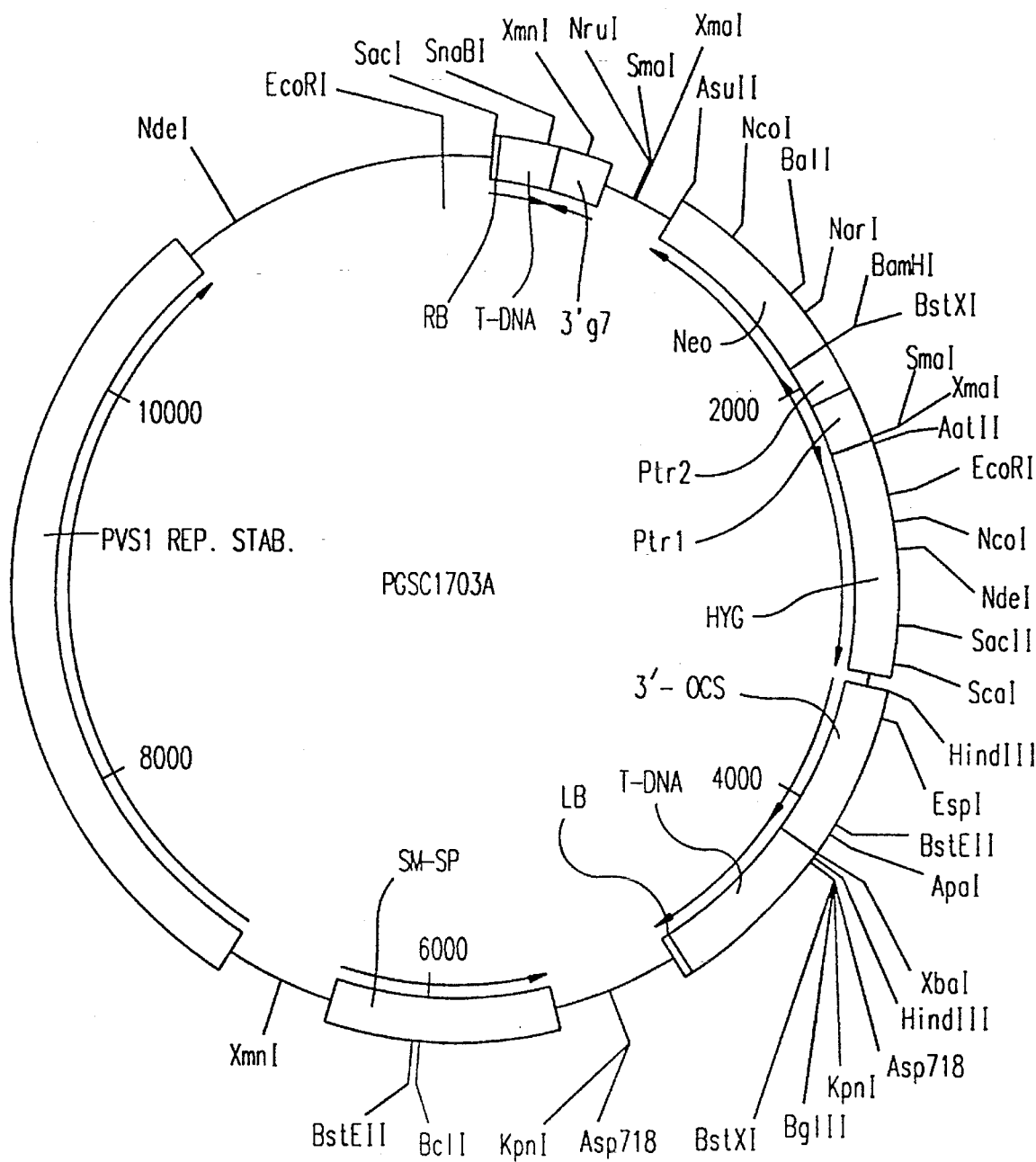

FIG. 16 represents the restriction map of pGSC1703A. The sequence is from a clone data bank. The sequence is from 1 to 11975. The sites are from 1 to 11975. The maximal occurrence frequency is 2. All enzymes are from ENZJB.

Figure 17A:
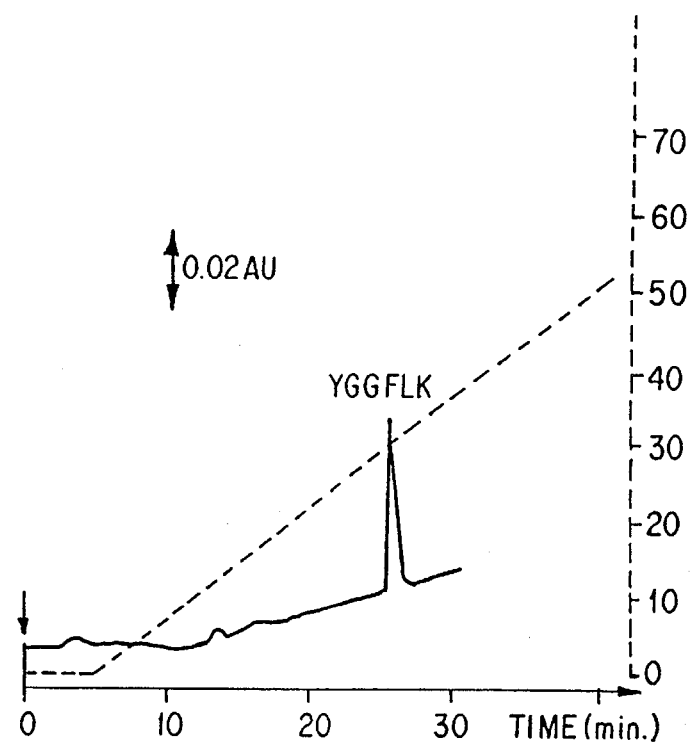

FIG. 17A represents a chromatogram of an aliquot of the synthetic peptide YGGFLK, used as marker, on a C4 column. The gradient (dashed line) is isocratic at 0% solvent between 0 and 5 minutes, and solvent B increases to 100% into 70 minutes. Solvent A: 0, 1% TFA in water; solvent B: 0, 1% TFA in 70% $CH_3CN$.

Figure 17B:
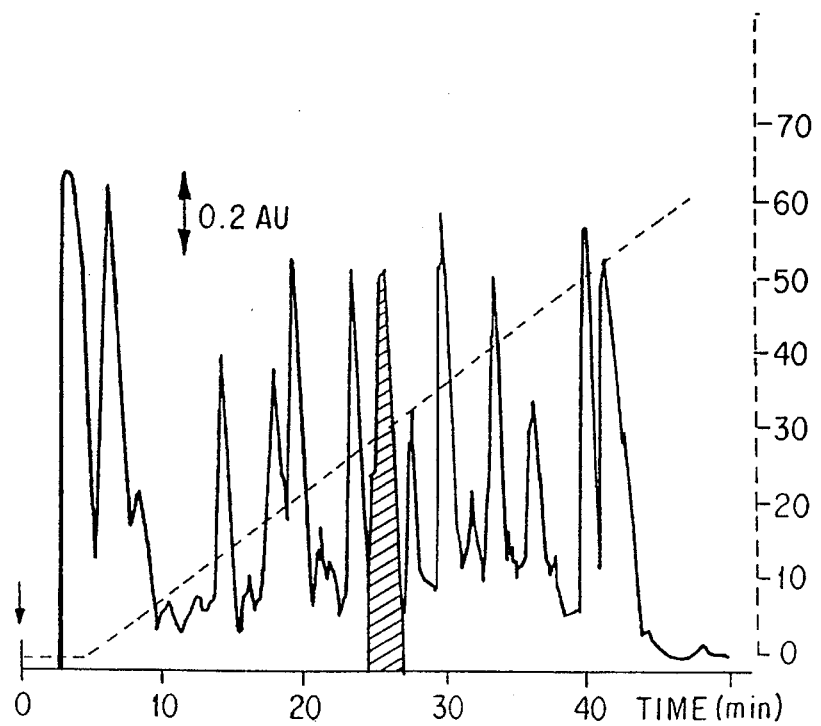

FIG. 17B represents a chromatogram of a tryptic digestion on oxidized 2S under the same conditions as done in FIG. 17A. The hatched peak was collected and subjected to further purification.

Figure 18A:
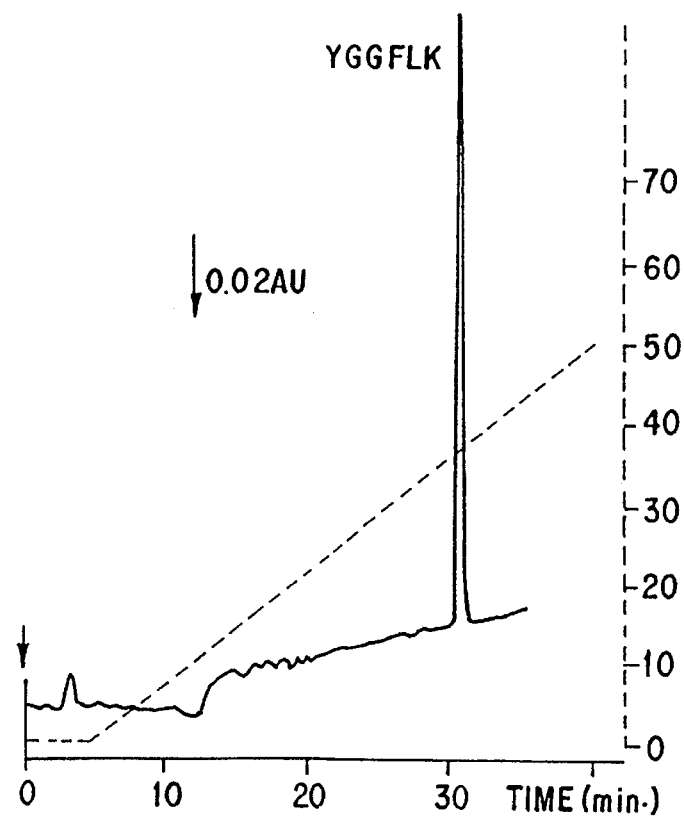

FIG. 18A represents a chromatogram of an aliquot of the synthetic peptide YGGFLK, used as a marker, on a C18 column. The gradient (dashed line) is isocratic at 0% solvent B between 0 and 5 minutes, and solvent B increases to 100% into 70 minutes. Solvent A: 0, 1% TFA in water; solvent B: 0, 1% TFA in 70% $CH_3CN$.

Figure 18B:
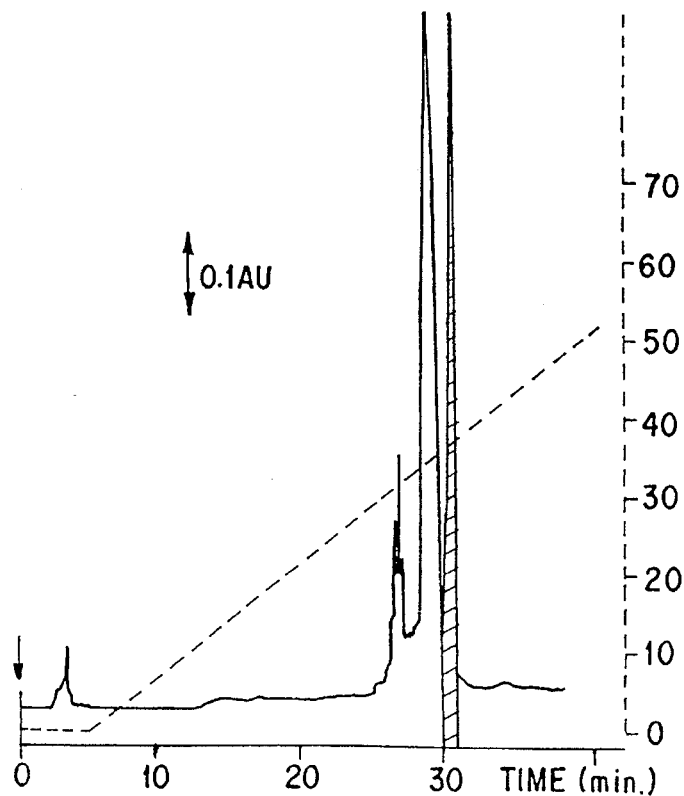
Figure 19A:
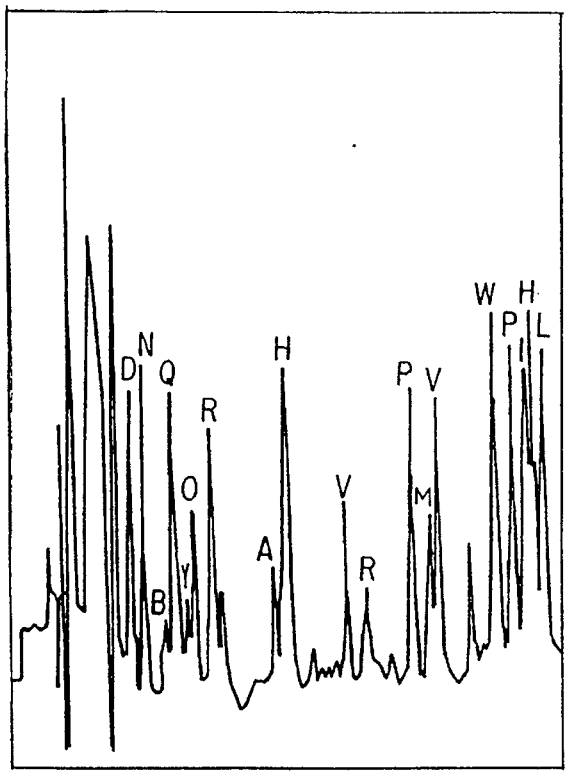
Figure 19B:
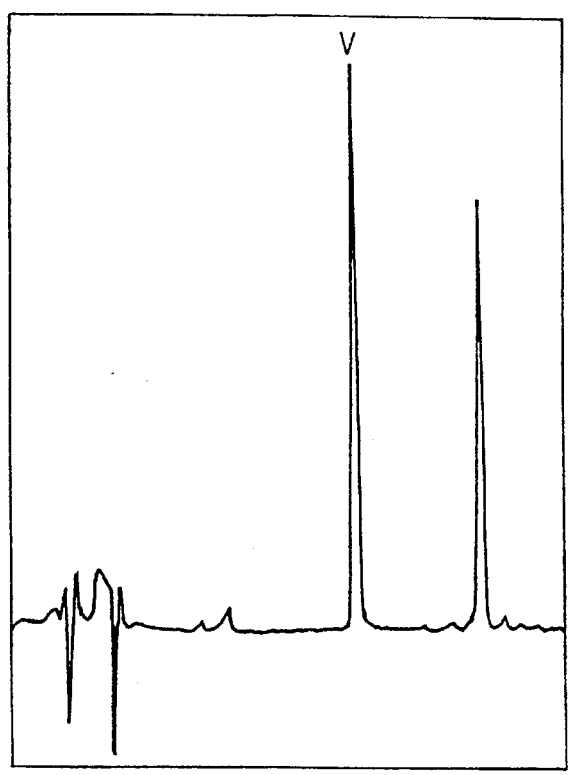
Figure 19C:
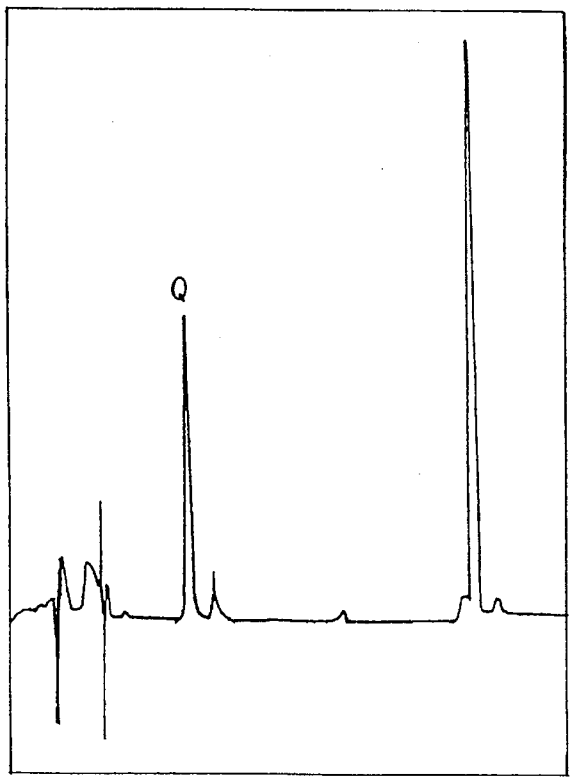
Figure 19D:
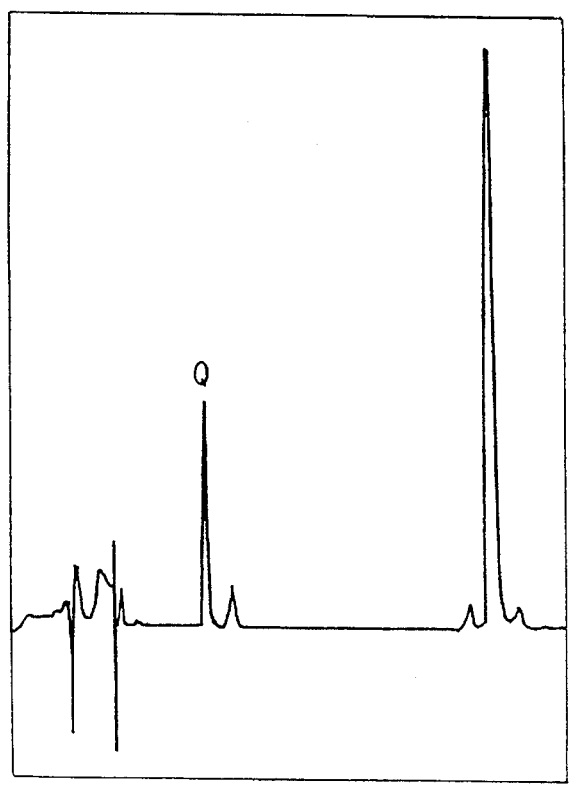
Figure 19G:
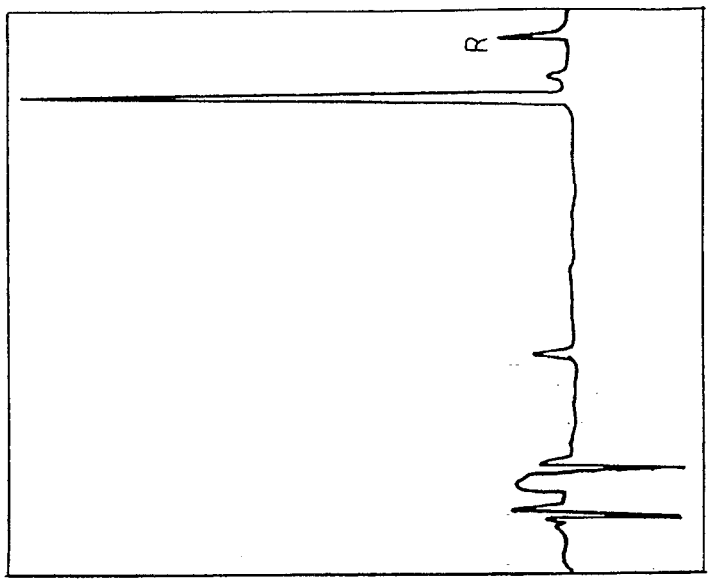
Figure 19F:
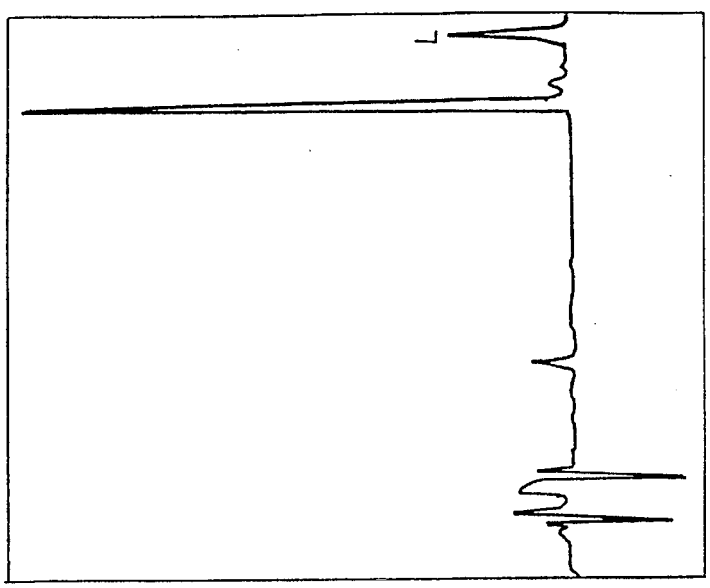
Figure 19E:
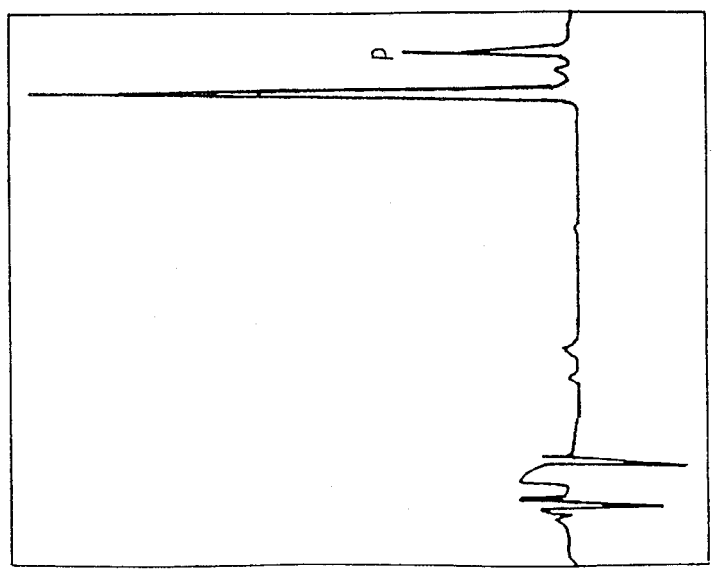

FIG. 18B represents the rechromatography on the C18 column of the YGGFLK containing peak obtained from HPLC on the C4 column (see FIG. 17B). The running conditions are the same as for FIG. 18A.

FIGS. 19A, 19B, 19C, 19D, 19E, 19F and 19G represent the results of the amino acid sequence determination on YGGFLK. The left corner box shows standard of PTH-amino acids (20 pmol each). The signal for cycles 1 to 6 is 8 times more attenuated as the reference.

Figure 20A:
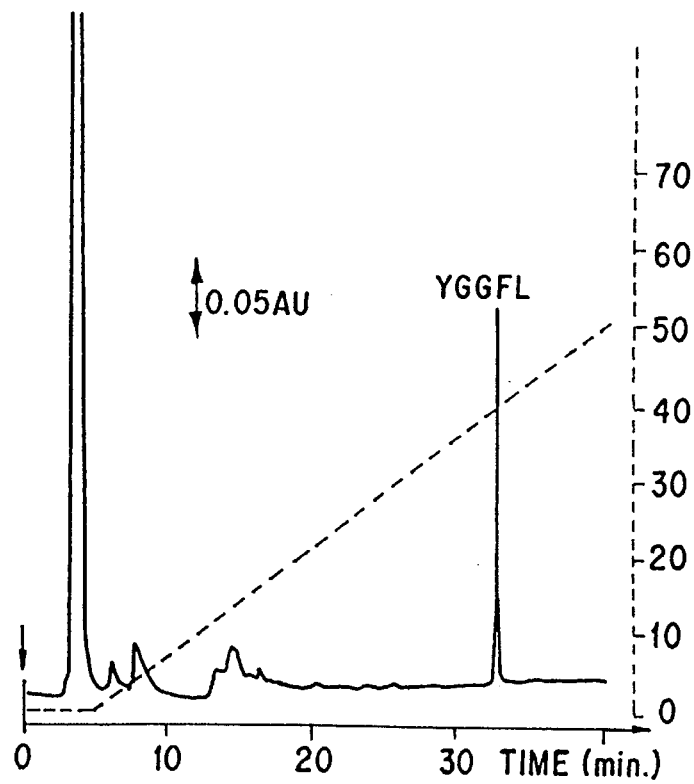

FIG. 20A represents a chromatogram showing the YGGFL peptide used as marker. This peptide is the result of a craboxypeptidase B digestion on the synthetic peptide YGGFLK. The running conditions are the same as in FIG. 17A.

Figure 20B:
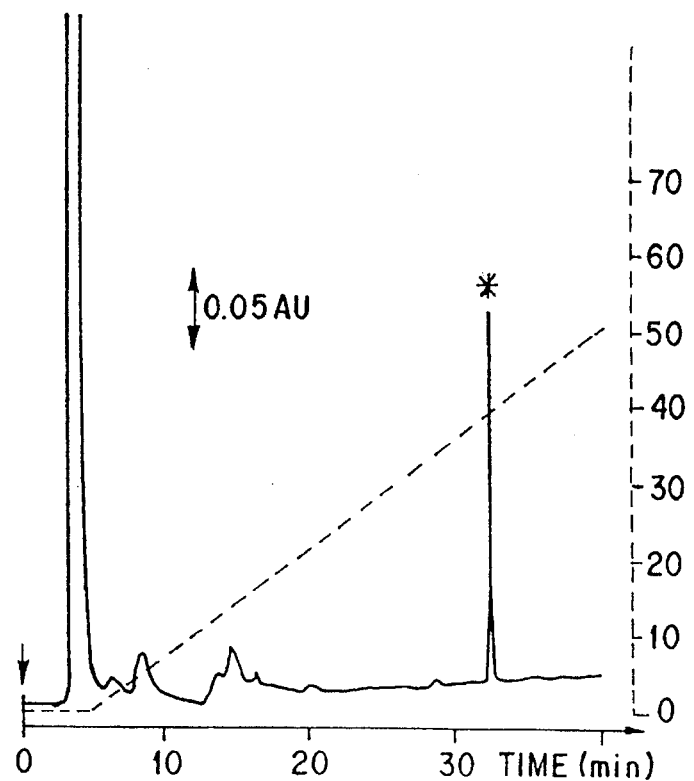

FIG. 20B shows the isolation of the IGGFL peptide, indicated with *, after carboxypeptidase B digestion on the YGGFLK peptide, that has been isolated from the plant material.

Figure 21:
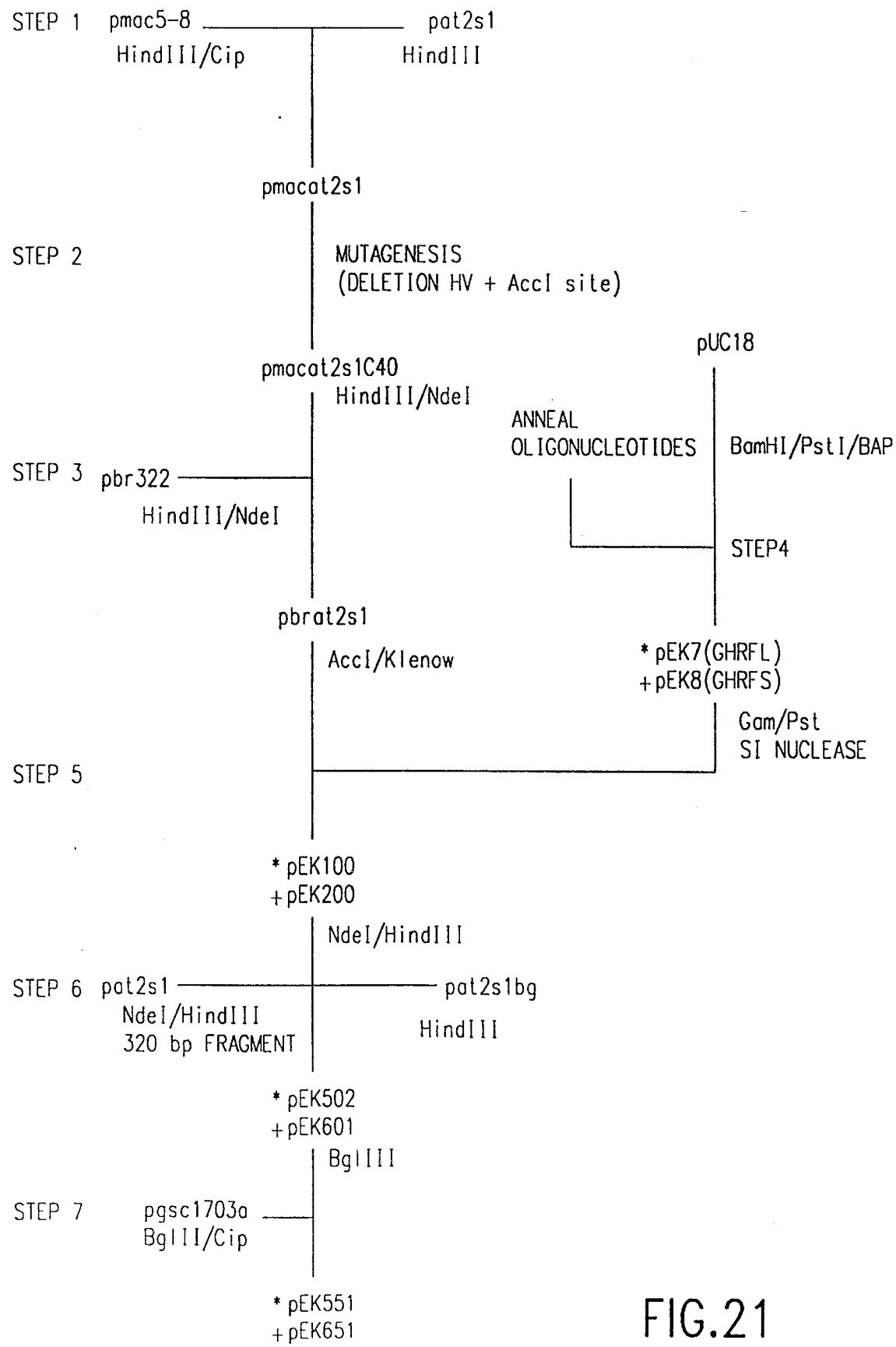

FIG. 21 shows diagrammatically the successive phases of the construction of a chimeric 2S albumins *Arabidopsis thaliania* gene including the deletion of practically all parts of the hypervariable region and its replacement by a AccI site, the insertion of the sequences encoding the GHRF and cleavage sites, given by way of example in the following disclosure, in the AccI site, particularly through site-directed mutagenesis and the cloning of said chimeric gene in plant vector suitable for plant transformation.

FIG. 22A shows the eight oligonucleotides used in the constructions of the GHRFS and GHRFL genes. The limits of the oligonucleotides are indicated by vertical lines, and the numbers above and below said oligonucleotides indicate their number. In oligonucleotides 4 and 8 the bases enclosed in the box are excluded, resulting in the gene encoding GHRFS. The peptide sequence of said GHRFS and GHRFL and the methionine sequences providing the CnBr cleavage sites are shown above the DNA sequence.

FIG. 22B shows the AccI site of the modified AT2S1 gene and the insertion of said GHRF's in said AccI site in such a way that the open reading frame is maintained.

EXAMPLE I

As a first example of the method described, a procedure is given for the production of Leu-enkephalin, a pentapeptide with opiate activity in the human brain and other neural tissues (Hughes et al., 1975a). A synthetic oligomer encoding the peptide and specific protease cleavage sites is substituted for part of the hypervariable region in a cDNA clone encoding the 2S albumin of Bertholletia excelsa (Brazil nut). This chimeric gene is fused to a fragment containing the promoter and signal peptide encoding regions of the soybean lectin gene. Lectin is a 7S albumin seed storage protein (Goldberg et al., 1983). The entire construct is transferred to tobacco plants using an Agrobacterium mediated transformation system. Plants are regenerated, and after flowering the seeds are collected and the 2S albumins purified. The enkephalin peptide is cleaved from the 2S albumin using the two specific proteases whose cleavage sites are built into the oligonucleotide, and then recovered using HPLC techniques.

1. cDNA synthesis and screening.

Total RNA is isolated from nearly mature seeds of the Brazil nut using the method described by Harris and Dure (1981). Poly A+ RNA is then isolated using oligo dT chromatography (Maniatis et al., 1982). cDNA synthesis and cloning can be done using any of several published methods (Maniatis et al., 1982: Okayama and Berg, 1982; Land et al., 1981; Gubler and Hoffman, 1983). In the present case, the 2S albumin from Brazil nut was sequenced (Ampe et al., 1986), and an oligonucleotide based on the amino acid sequence was constructed. This was used to screen a cDNA library made using the method of Maniatis et al. (1982). The resulting clone proved to be too short, and a second library was made using the method of Gubler and Hoffman (1983) and screened using the first, shorter cDNA clone. A DNA recombinant containing the Brazil nut 2S-albumin sequence was isolated. The latter was further cloned in plasmid pUC 18. Yanisch-Perron, C., Vieira, J. and Massino, J. (1985) Gene 33, pp. 103–119.

The recovered plasmid was designated pBN 2S1. The derived protein sequence, the DNA sequence, the region to be substituted, and the relevant restriction sites are shown in FIG. 4.

The deduced protein sequence (obtained from plasmid pBN2S1) is shown above the DNA sequence, and the proteolytic processing sites are indicated (in FIG. 4). The end of the signal sequence is indicated by a Restriction sites used in the construction in FIG. 6, 7, 10, 11 and 12 are indicated. The polylinker of the cloning vector is shown in order to indicate the PstI site used in the latter part of the construction. The protein and DNA sequences of the peptide to be inserted are shown below the cDNA sequence, as well as the rest of the oligonucleotide to be used in the mutagenesis. During the mutagenesis procedure the oligonucleotide shown is hybridized to the opposite strand of the cDNA (see FIG. 10). 2. Construction of a chimeric gene.

The 2S albumin gene is first fused to the DNA fragment encoding the promotor and signal peptide of the soybean lectin gene. The cleavage point of the signal peptide in both lectin and Brazil nut is derived from standard consensus sequences (Perlman and Halvorson, 1983). The relevant sequences are shown hereafter as well as in FIG. 4.

```
        A    N   *S    A
       GCA  AAC TCA  GCG
       CGT  TTG AGT  CGC
              Ddei
              C/TNAG pSOYLEA 1
        A    N    S    D    L
       GCA  AAC  TCA  GAT  CTG
       CGT  TTG  AGT  CTA  GAC
                     BglII
                     A/GATCT pBN2S1       *
        T    A    F    R    A    T
       ACC  GCC  TTC  CGG  GCC  ACC
       TCC  CGG  AAG  GCC  CGG  TGG
              BglII
              GCCNNNN/NGGC
```

The protein and double stranded DNA sequences in the regions of the signal peptide/mature protein sequences in the plasmids pLe1, pSOYLEA 1 and pBN2S1 are shown in FIG. 5. The positions and recognition sites of the restriction sites used in the constructions shown in the drawings are indicated. * indicates the protein cleavage site at the end of the signal sequence.

The starting point for the construction is the plasmid pLe1 (Okamuro et al., 1987), which contains a soybean genomic HindIII fragment. This fragment includes the entire soybean lectin gene, its promotor, and sequences upstream of the promoter which may be important for seed specific expression. From this fragment a suitable soybean lectin promotor/signal sequence cassette was constructed as shown in FIG. 6a. A DdeI site is present at the end of the sequence encoding the signal sequence (SS), and its cleavage site (C/TCAG) corresponds to the processing site. To obtain a useful restriction site at this processing site, a KpnI-DdeI fragment of the SS sequence (hereafter designated as "ss") is isolated from pLE1 and cloned into pLK57 (Botterman, 1986) itself linearized with KpnI and BglII. The DdeI and BglII ends are filled in with Klenow DNA Polymerase I. this reconstructs the BglII site (A/GATCT), whose cleavage site now corresponds to the signal sequence processing site (see FIG. 6, 7a). The plasmid so-obtained, pSOYLEA1, thus consists of plasmid pLK57 in which the KpnI-DdeI fragment of the SS sequence (ss) initially contained in pLE1 is substituted for the initial KpnI-BglII fragment of pLK57. A HindIII site is placed in front of this fragment by substituting a KpnI-PstI fragment containing said HindIII site from pLK69 (Botterman, 1986) for the PstI-KpnI fragment designated by (1) in pSoyLea1 as shown diagrammatically in FIG. 4. this intermediate construction is called pSoyLea2. In a second step the lectin promoter is reconstructed by inserting the HindIII-KpnI fragment (2) of pLE1 in pSoyLea2. As there is another BglII site present upstream of the promoter fragment, the lectin promoter/signal sequence cassette is now present as a BglII-BglII fragment in the plasmid pSoyLea3.

This cassette is now fused, in register, with a 205 bp Brazil nut cDNA fragment of plasmid pBN2S1 and containing the coding sequences for the Brazil nut pro-2S albumin (i.e., the entire precursor molecule with the exception of the signal sequence). This is done as shown in FIG. 5. The 205bp fragment obtained after digestion of the cDNA clone pBN2S1 (FIG. 4) with BglI, treatment with Klenow DNA Polymerase I to resect the BglI protruding ends, and digestion with PstI is cloned into pUC18 (Yannish-Perron et al., 1985) which has been linearized by digestion with SmaI and PstI. The resulting plasmid, pUC18-BN1, is digested with both EcoRI and AvaI, both ends filled in, and religated. This results in the reconstruction of a new plasmid, designated pUC18-BN2, containing the desired Brazil nut coding sequence with an EcoRI site at the beginning (FIG. 7).

To fuse the Brazil nut coding sequences in register to the lectin promoter/signal sequence cassette, pUC18-BN2 is digested with EcoRI and the ends partially filled in using Klenow enzyme in the presence of dATP alone. The remaining overhanging nucleotides are removed with S1 nuclease, after which a PstI digest is carried out. This yields a fragment with one blunt end and one PstI digested end. The lectin promoter/signal sequence fragment is taken from pSoyLea1 (FIG. 7) as an EcoRI-BglII fragment with filled in BglII ends. The two fragments are ligated together with PstI-EcoRI digested pUC18. This results in pUC18SLBN1, with a reconstructed BglII site at the junction of the signal peptide encoding sequence and the Brazil nut sequences (FIG. 7). pUC18SLBN1 thus consists of the pUC18 plasmid in which there have been inserted the BglII-EcoRI fragment (shown by (3) on FIG. 6) of pSoyLea1 and, upstream thereof in the direction of transcription the EcoRI-Pst-EcoRI fragment supplied by pUC18BN2 and containing the 205 bp cDNA coding sequence for the Brazil nut pro-2S albumin.

However, the reading frame is not properly maintained. In order to correct this, the plasmid is linearized with BglII, treated with S1 nuclease, and religated. This intermediate is designated pUC18SLBN2. The construction is finally completed in two steps by inserting the KpnI fragment carrying the 5' part of the promoter from pSoyLea3, yielding pUC18SLBN3, and inserting into the latter the PstI fragment containing the 3' part of the Brazil nut cDNA from pBN2S1. The resulting final construction, pUC18SLBN4, contains the lectin promoter/signal sequence—Brazil nut cDNA sequence fusion contained within a BamHI fragment.

3. Substitution of part of the hypervariable region with sequences encoding enkephalin and protease cleavage sites.

The Leu-enkephalin peptide has the sequence Tyr-Gly-Gly-Phe-Leu (Hughes et al., 1975b). In order to be able to recover the intact polypeptide from the hybrid 2S albumin after purification, codons encoding Lysine are placed on either side of the enkephalin coding sequences. This allows the subsequent cleavage of the enkephalin polypeptide from the 2S albumin with the endopeptidases endolysin-C and carboxypeptidase B in the downstream processing steps. Finally, in order for the oligonucleotide to be capable of hybridizing to the gapped duplex molecule during mutagenesis (see below), extra sequences complementary to the Brazil nut sequences to be retained are included. The exact sequence of the oligonucleotide, determined after the study of codon usage in several plant storage protein genes, is

5'-GCAACAGGAGAAGTACGGTGGATTCTTGAAGCAGATGCG-3'.

The substitution of part of the sequence encoding the hypervariable region of the Brazil nut 2S albumin is done using site-directed mutagenesis with the oligonucleotide as primer (FIGS. 4 and 10). The system of Stanssens et al. (1987) is used.

The Stanssens et al method is illustrated in FIG. 9 and recalled hereinafter. It makes use of plasmid pMac5-8 whose restriction and genetic map is shown in FIG. 8 and whose main features are also recalled hereinafter.

The positions of the relevant genetic loci of pMac5-8 are indicated in FIG. 8. The arrows denote their functional orientation. fdT: central transcription terminator of phage fd; f1-ORI: origin of replication of filamentous phage f1; ORI: ColE1-type origin of replication; BLA/$Ap^R$: region coding for β-lactamase; CAT/$Cm^R$: region coding for chloramphenicol acetyl transferase. The positions of the amber mutations present in pMc5-8 (the bla-am gene does not contain the ScaI site) and pMc5–8 (cat-am; the mutation eliminates the unique PvuII site) are indicated. Suppression of the cat amber mutation in both supE and supF hosts results in resistance to at least 25 μg/ml Cm. pMc5–8 confers resistance to ±20 μg/ml and 100 μg/ml Ap upon amber-suppression in supE and supF strains respectively. The EcoRI, BalI and NcoI sites present in the wild-type cat gene (indicated with an asterisk) have been removed using mutagenesis techniques.

The principle of the Stanssens method as also applied to the substitution of the Leu-enkephalin peptide for the selected hypervariable region of 2S-albumin region here examplified, as described hereafter, is also first recalled hereafter:

Essentially the mutagenesis round used for the above mentioned substitution is ran as follows. Reference is made to FIG. 9, in which the amber mutations in the Ap and Cm selectable markers are shown by closed circles. The symbol ✗ represents the mutagenic oligonucleotide. The mutation itself is indicated by an arrowhead.

The individual steps of the process are as follows:

Cloning of the target DNA fragment into pMa5–8 (I). This vector carries on amber mutation in the $Cm^R$ gene and specifies resistance to ampicillin.

Preparation of single stranded DNA of this recombinant (II) from pseudoviral particles.

Preparation of a restriction fragment from the complementary pMc-type plasmid (III). pMc-type vectors contain the wild-type $Cm^R$ gene while an amber mutation is incorporated in the Ap resistance marker.

Construction of gap duplex DNA (hereinafter called gdDNA) gdDNA (IV) by in vitro DNA/DNA hybridization. In the gdDNA the target sequences are exposed as single stranded DNA. Preparative purification of the gdDNA from the other components of the hybridization mixture is not necessary.

Annealing of the synthetic oligonucleotide to the gdDNA (V).

Filling in the remaining gaps and sealing of the nicks by a simultaneous in vitro DNA polymerase/DNA ligase reaction (VI).

Transformation of a mutS host, i.e., a strain deficient in mismatch repair, selecting for Cm resistance. This results in production of a mixed plasmid progeny (VII).

Elimination of progeny deriving from the template strand (pMa-type) by retransformation of a host unable to suppress amber mutations (VIII). Selection for Cm resistance results in enrichment of the progeny derived from the gapped strand, i.e., the strand into which the mutagenic oligonucleotide has been incorporated.

Screening of the clones resulting from the retransformation for the presence of the desired mutation.

In the mutagenesis experiment, depicted in FIG. 9, Cm resistance is used as an indirect selection for the synthetic marker. Obviously, an experiment can be set up such that the Ap selectable marker is exploited. In the latter case the single stranded template (II) and the fragment (III) are the pMc- and pMa-type, respectively. A single mutagenesis step not only results in introduction of the desired mutation but also in conversion of the plasmid from pMa-type to pMc-type or vice versa. Thus, cycling between these two configurations (involving alternate selection for resistance to ampicillin or chloramphenicol) can be used to construct multiple mutations in a target sequence in the course of consecutive mutagenesis rounds.

Reverting now to the present example relative to the substitution of part of the sequence encoding the hypervariable region of the Brazil nut 2S albumin, the Stanssens et al system is thus applied as follows:

The PstI-EcoRI fragment of the chimeric gene containing the region of interest (see FIGS. 10, 11 and also FIG. 4) is inserted in a pMa vector which carries an intact beta-lactamase gene and a chloramphenicol acetyltransferase gene with an amber mutation FIG. 10, so that the starting plasmid confers only ampicillin resistance but not chloramphenicol resistance. Single stranded DNA (representing the opposite strand to that shown in FIG. 4) is prepared and annealed with the EcoRI-PstI linearized form of a pMc type plasmid, yielding a gapped duplex molecule. The oligonucleotide is annealed to this gapped duplex. The single stranded gaps are filled with Klenow DNA polymerase I, ligated, and the mixture transformed into the appropriate host. Clones carrying the desired mutation will be ampicillin sensitive but chloramphenicol resistant. Transformants resistant to chloramphenicol are selected and analyzed by DNA sequencing. Finally, the hybrid gene fragment is inserted back into the lectin/Brazil nut chimera by replacement of the PstI-NcoI fragment in pUC18SLBN4 with the mutagenised one from pMC58BN (FIG. 11). The resulting plasmid, pUC18SLBN5, contains the lectin promoter and signal sequence fused to a hybrid Brazil nut-enkephalin gene, all as a BamHI fragment.

4. Transformation of tobacco plants.

The BamHI fragment containing the chimeric gene is inserted into the BamHI site of the binary vector pGSC1702 (FIG. 12). This vector contains functions for selection and stability in both *E. coli* and *A. tumefaciens*, as well as a T-DNA fragment for the transfer of foreign DNA into plant genomes (Deblaere et al., 1987). The latter consists of the terminal repeat sequences of the octopine T-region. The BamHI site into which the fragment is cloned is situated in front of the polyadenylation signal of the T-DNA gene 7. A chimeric gene consisting of the nopaline synthase (nos) promoter, the neomycin phosphotransferase protein coding region (neo) and the 3' end of the OCS gene is present, so that transformed plants are rendered kanamycin resistant. Using standard procedures (Deblaere et al., 1987), the plasmid is transferred to the Agrobacterium strain C58C1Rif carrying the plasmid pGV2260. The latter provides in trans the vir gene functions required for successful transfer of the T-DNA region to the plant genome. This Agrobacterium is then used to transform tobacco plants of the strain SR1 using standard procedures (Deblaere et al., 1987). Calli are selected on 100 µg/ml kanamycin, and resistant calli used to regenerate plants. DNA prepared from these plants is checked for the presence of the hybrid gene by hybridization with the Brazil nut 2S albumin cDNA clone or the oligonucleotide. Positive plants are grown and processed as described below.

5. Purification of 2S albumins from seeds.

Positive plants are grown to seed, which takes about 15 weeks. Seeds of individual plants are harvested and homogenized in dry ice, and extracted with hexane. The remaining residue is taken up in Laemmli sample buffer, boiled, and put on an SDS polyacrylamide gel (Laemli, 1970). Separated proteins are electroblotted onto nitrocellulose sheets (Towbin et al., 1979) and assayed with a commercially available polyclonal antibody of the Leu-enkephalin antigen (UCB cat. £i72/001, ib72/002).

Using the immunological assays above, strongly positive plants are selected. They are then grown in larger quantities and seeds harvested. A hexane powder is prepared and extracted with high salt buffer (0.5M NaCl, 0.05M Na-phosphate pH 7.2). This extract is then dialysed against water, clarified by centrifugation (50,000xg for 30 min), and the supernatant further purified by gel filtration over a Sephadex G-75 column run in the same high salt buffer. The proteins are further purified from non-ionic, non protein material ion exchange chromatogrpahy on a DEAE-Cellulose column. Fractions containing the 2S protein mixture are then combined, dialysed against 0.5% $NH_4HCO_3$, and lyophilised.

6. Recovery of Leu-enkephalin.

The mixture of purified endogenous 2S storage proteins and hybrid 2S proteins are digested with endo-Lys-C. In order to ensure efficient proteolytic degradation, the 2S proteins are first oxidized with performic acid (Hits, 1956). The oxidation step opens the disulfide bridges and denatures the protein. Since Leu-enkephalin does not contain amino acid residues which may react with performic acid, the opiate will not be changed by this treatment. Endo-Lys-C digested is carried out in an 0.5% $NH_4HCO_3$ solution for 12 hours at 37° C. and terminated by lyophilization. This digestion liberates the Leu-enkephalin, but still attached to the C terminal Lysine residue. Since the hybrid protein contains very few other lysine residues, the number of endo-Lys-C peptides is very small, simplifying further purification of the peptide. The enkephalin-Lys peptides are purified by HPLC reversed phase chromatography using a C18 column (e.g., that commercialized under the tradermard VYDAC). The gradient consists of 0.1% trifluoroacetic acid as initial solvent (A) and 70% acetonitrile in 0.1% trifluoroacetic acid as diluter solvent (B). A gradient of 1.5% solvent B in A per minute is used under the conditions disclosed by Ampe et al., (1987). The purified enkephalin-Lys peptide is identified by amino acid analysis and/or by immunological techniques. It is further treated by carboxypeptidase B as disclosed by Ambler, (1972) in order to remove the carboxyl terminal Lysine residue. Finally, the separation and purification of the opiod peptide is finally achieved by reversed phase HPLC chromatography according to the method disclosed by Lewis et al., (1979).

Other methods are available, as illustrated in Example II.

7. Assay of Leu-enkephalin biological activity.

Enkephalins inhibit [$^3$H]-naloxone binding in sodium-free homogenates of guinea pig brain. Opiod acivity can be assayed as the ability to inhibit specific [$^3$H]-naloxone binding to rat brain membranes (Pasternak et al., 1975) as previously described (Simantov et al., 1976). One unit of opiod activity "enkephalin" was defined as that amount that yields 50% occupancy in a 200 µl assay (Colquhaun et al., 1973).

EXAMPLE II

As a demonstration of the flexibility of the technique, a procedure for the production of Leu-enkephalin using a different 2S albumin is given. In this case, instead of using a cDNA clone from *Bertholletia excelsa* as basis for the construction, a genomic clone isolated from *Arabisopsis thaliana* is used. Since a genomic clone is used the gene's own promoter is used, simplifying the construction considerably. To further demonstrate the generality of the technique, the altered 2S albumin gene is brought to expression in three different plants: tobacco, *Arabidopsis* and *Brassica*

*napis,* a relative of Arabidopsis which also has a 2S albumin (see introduction). Many of the details of this example are similar to the previous one and are thus described more briefly.

1. Cloning of the *Arabidopsis thaliana* 2S albumin gene.

Given the ease of purification of 2S albumin (see introduction, example 1), the most straightforward way to clone the Arabidopsis 2S albumin gene is to construct oligonucleotide probes based on the protein sequence. The protein sequence was determined by standard techniques, essentially in the same way as that of the Brazil nut 2S albumin (Ampe et al., 1986). FIG. 13 shows the sequence of the 1 kb HindIII fragment containing the *Arabidopsis thaliana* 2S albumin gene. The deduced protein sequence is shown above the DNA sequence, and proteolytic processing sites are indicated. The end of the signal sequence is indicated by a, and SSU indicates small subunit. The protein and DNA sequences of the peptide to be inserted are shown below the cDNA sequence, as well as the rest of the oligonucleotide to be used in the mutagenesis. During the mutagenesis procedure the oligonucleotide shown is hybridized to the opposite strand of the DNA sequence shown. The Nde I site used to check the orientation of the HindIII fragment during the construction is underlined (bp-117). The numbering system is such that the A of initiation codon is taken as base pair 1.

The difficulty in using oligonucleotide probes is that more than one codon can encode an amino acid, so that unambiguous determination of the DNA sequence is not possible from the protein sequence. Hence the base inosine was used at ambiguous positions. The structure of inosine is such that while it does not increase the strength of a hybridization, it does not decrease it either (Ohtsuka et al., 1985; Takahashi et al., 1985). On this basis, three oligonucleotide probes were designed as shown in FIG. 14. The protein sequence of the large sub-unit of the 2S albumin of *Arabidopsis thaliana*. Under the protein sequence are the sequences of the oligonucleotides used as hybridization probes to clone the gene. I designates Inosine.

The three oligonucleotides were used to screen a genomic library of Arabidopsis DNA constructed in the phage Charon 35 (Loenen and Blattner, 1983) using standard methods (Maniatis et al., 1982; Benton and Davis, 1977). The oligonucleotides were kinased (Miller and Barnes, 1986), and hybridizations were done in 5X SSPE (Maniatis et al., 1982), 0.1% SDS, 0.02% Ficoll, 0.02% Polyvinylpyrolidine, and 50 µg/ml sonicated herring sperm DNA at 45° C. Filters were washed in 5X SSPE, 0.1% SDS at 45 degrees for 4–8 minutes. Using these conditions, a clone was isolated which hybridized with all three oligonucleotide probes. Appropriate regions were subcloned into pUC18 (Yanisch-Perron et al., 1985) using standard techniques (Maniatis et al., 1982) and sequenced using the methodology of Maxam and Gilbert (1980). The sequence of the region containing the gene is shown in FIG. 13.

2. Substitution of part of the hypervariable region with sequences encoding enkephalin and protease cleavage sites.

The gene isolated above was used directly for construction of a Leu-enkephalin/2S albumin chimera. As in the first example, an oligo was designed incorporating the Leu-enkephalin sequence and lysine encoding codons on either side of it, in order to be able to recover the enkephalin polypeptide in the downstream processing steps, and extra sequences complementary to the flanking Arabidopsis sequences in order for the oligonucleotide to be able to hybridize to the gapped duplex molecule during the mutagenesis. The resultant oligonucleotide has the sequence:

5'-CAAGCTGCCAAGTACGGTGGATTCTTGAAGCAGCACCAAC-3' its position in the sequence is shown in FIG. 8.

The region containing the gene and sufficient flanking regions to include all necessary regulatory signals is contained on a 3.6 kb BglII fragment, inserted in the cloning vector pJB65 (Botterman et al., 1987). The clone is called pAT2S1Bg. The region to be mutagenized is contained on 1 kb Hind III fragment within the 3.6 kb BglII fragment, and this smaller fragment is inserted into the HindIII site of the pMa5–8 vector of Stanssens et al., (1987) (FIG. 5c). The orientation is checked using an asymmetric NdeI site (FIG. 8). The mutagenesis is carried out using exactly the strategy described in step 3 of example 1. Subsequently the hybrid gene is reinserted into the larger fragment with the mutagenized one using standard techniques (Maniatis et al., 1982). The orientation is again checked using the NdeI site.

3. Transformation of plants.

The BglII fragment containing the hybrid gene and sufficient flanking sequences both 5' and 3' to the coding region to insure that appropriate signals for gene regulation are present is inserted into the BamHI site of the same binary vector, pGSC1702, used in example 1 (FIG. 12). This vector is described in section 4 of example 1. Transformation of tobacco plants is done exactly as described there. The techniques for transformation of *Arabidopsis thaliana* and *Brassica napus* are such that exactly the same construction, in the same vector, can be used. After mobilization to *Agrobacterium tumefaciens* as described in section 4 of example 1, the procedures of Llyod et al., (1986) and Klimaszewska et al. (1985) are used for transformation of Arabidopsis and Brassica respectively. In each case, as for tobacco, calli can be selected on 100 µg/ml kanamycin, and resistant calli used to regenerate plants. DNA prepared from such plants is checked for the presence of the hybrid gene by hybridization with the oligonucleotide used in the mutagenesis (In the case of tobacco and Brassica, larger portions of the hybrid construct could be used, but in the case of the Arabidopsis these would hybridize with the endogenous gene.).

In the embodiment of the invention, BglII fragment containing the hybrid gene and sufficient flanking sequences both 5' and 3' to the coding region to insure that appropriate signals for gene regulation are present is inserted into the BglII site of the binary vectors pGSC1703 (FIG. 15) or pGSC1703A (FIG. 16). pGSC1703 contains functions for selection in both *E. coli* and Agrobacterium, as well as the T-DNA fragments allowing the transfer of foreign DNA into plant genomes (Deblaere et al., 1987) It further contains the bidirectional promotor TR (Velten et al., 1984) with the neomycine phosphotransferase protein coding region (NPTII) and the 3' end of the ocs gene. It do not contain a gene encoding ampicillin resistance, as pGSC1702 does, so that carbenicillin as well as claforan can be used to kill the Agrobacteria after the infection step. Vector pGSC1703A contains the same functions as vector pGSC1703, with an additional gene encoding hygromycine transferase. This allows the selection of the transformants on both kanamycin as hygromycine. Transformation of tobacco plants is done exactly as described in section 4 of Example I, whereby the hybrid gene is inserted into the plant transformation vector pGSC1703. Transformation of *Arabidopsis thaliana* and *Brassica napus* were done with pGSC1703A in which the hybrid AT2S1 gene has been inserted. After mobilization to *Agrobacterium tumefaciens* C58C1Rif carrying the plasmid pMP90 (Koncz and Schell, 1986), which latter provides in trans and vir gene functions but which do not carry a gene encoding ampicillin resistance, the procedures of Lloyd et al., (1986) and Klimaszewska et al. (1985) are used for transformation of Arabidopsis and Brassica respectively. Carbenicillin is used to kill the Agrobacterium after co-cultivation occured. In each case, as for tobacco, calli can be selected on 100 µg/ml kanamycin, and resistant calli used to regenerate plants. DNA prepared from such plants is checked for the presence of the hybrid gene by hybridization with the oligonucleotide used in the mutagenesis. (In the case of tobacco, larger portions of the hybrid construct could be used, but in the case of Brassica and Arabidopsis these would hybridize with the endogenous gene.)

4. Purification of 2S albumins from seeds and further processing

Positive plants from each species are grown to seed. In the case of tobacco this takes about 15 weeks, while for Arabidopsis and Brassica approximately 6 weeks and 3 months respectively are required. Use of different varieties may alter these periods. Purification of 2S albumins from seeds, recovery of the Leu-enkephalin, and assaying the latter for biological activity are done as follows.

Methods Used for the Isolation of Enkephalin from Arabidopsis Seeds

Two methods were used to isolate Enkephalin from Arabidopsis seeds. First, a small amount of seeds isolated from several individual transformants was screened for the presence of chimeric 2S albumins. This is done because, as described by Jones et al., (1985), expression of introduced genes may vary widely between individual transformants. Seeds from individual plants seen by this preliminary screening were then used to isolate larger amounts and determine yields more accurately. Both procedures are described below.

A) Fast screening procedure for Enkephalin-containing 2S proteins

Seeds of individual plants (approximately 50 mg) were collected and ground in an Eppendorf tube with a small plastic grinder shaped to fit the tube. No dry ice is used in this procedure. The resulting paste was extracted three times with 1 ml of heptane and the remaining residue dried. The powder was suspended in 0.2 ml of 1M NaCl and centrifuged for 5 min in an Eppendorf centrifuge. This extraction was repeated three times and the supernatants combined, giving a total volume of approximately 0.5 ml. This solution was diluted 20 fold with water, giving a final NaCl concentration of 0.05M. This was stored overnight at 4° C. and then spun at 5000 rpm in a Sorvall SS-34 rotor for 40 min. The resulting supernatant was passed over a disposable C18 cartridge (SEP-PAC, Millipore, Milford, Mass., U.S.A.). The cartridges were loaded by injecting the 10 ml supernatant with a syringe through the columns at a rate of 5 ml/min. The cartridge was then washed with 2 ml of 0.1% TFA and proteins were desorbed by a step elution with 2 ml portions of a 0.1% TFA solution containing 7%, 14%, 21% etc. up to 70% acetonitrile. The fractions eluting in the range from 28% to 49% acetonitrile are enriched for 2S albumins as judged by SDS-polyacrylamide gel analysis performed on aliquots taken from the different fractions. The 2S albumin-containing fractions were combined and dried in a Speed Vac concentrator (Savant Instruments).

The combined fractions were reconstituted in 0.95 ml 0.1% TFA in water, filtered through an HV-4 Millex filter (Millipore), and applied to a reversed phase $C_4$ column 25 cm in length and 0.46 cm in diameter (Vydac 214TP54, pore size 300 angstrom, particle size 5 µm). The HPLC equipment consisted of 2 pumps (model 510), a gradient controller (model 680) and an LC spectrophotometer detector (Lambda-Max model 481, all from Waters, Milford, Mass., U.S.A.). The gradients were run as follows: Solution A was 0.1% TFA in $H_2O$, solution B 0.1% TFA in 70% $CH_3CN$. For 5 minutes, a solution of 0% B, 100% A was run over the column, after which the concentration of B was raised to 100% in a linear fashion over 70 minutes. The column eluate was detected by absorbance at 214 nm. The fractions containing 2S albumins were collected and dried in a Speed Vac concentrator.

In order to obtain a more complete digestion with proteases it is recommended that the proteins be denatured by oxidizing the disulfide bridges with performic acid. This is done by adding 0.5 ml of a solution made by mixing 9 ml of formic acid and 1 ml of 30% $H_2O_2$ at room temperature. The solution was made 2 hours before use. The reaction is allowed to proceed for 30 min at 0° C. and terminated by drying in a Speed Vac concentrator. Traces of remaining performic acid were removed by twice adding 500 µl of water and lyophilizing the sample.

The residue was redissolved in 0.75 ml of 0.1M Tris-HCl pH 8.5 after which 4 µg of TPCK-treated trypsin (Worthington) was added. The reaction was placed at 37° C. for 3 hours, after which it was terminated by the addition of 10 µl of TFA and stored at −20° C. prior to analysis. The resulting peptide mixture is separated by HPLC using the columns and gradient mixtures described above. As a standard, a peptide of the same sequence as that expected (YGGFLK) was synthesized using standard techniques on a Biolynx 4175 peptide synthesizer (LKB). This peptide was run over the column and the retention time determined. The mixture of peptides resulting from the trypsin digest was then loaded on the same column and peptides with the same retention time as the standard were collected, dried, and reloaded on a C18-reversed phase column. The elution time of the marker peptide again served as a reference for the correct position of the enkephalin containing peptide. The identity of this peptide was confirmed by amino acid sequencing, which also allowed a rough quantitation. Four plants of the six transformants analyzed were shown to contain significant quantities of Leu-enkephalin. By way of example the detailed analysis and processing steps are given below for one of these said four plants.

B) Larger Scale Isolation and Processing of Enkephalin from Arabidopsis Seeds

Grinding and initial extraction 2.11 g of seeds from said plant were ground in a mortar in dry ice. Lipids were removed from the resulting powder by extracting three times with 5 ml of heptane. The resulting residue was dried.

Protein extraction

The powder was dissolved in approximately 4 ml of 1.0M NaCl. The resulting paste was spun in an SS-34 rotor at 17,500 rpm for 40 min. After each spin the supernatant was transferred to a fresh tube and the pellet again resuspended in 4 ml of 1.0M NaCl. This procedure was repeated three times. The three supernatants (12 ml total) were passed through a 0.45 µm filter (HA, Millipore).

Isolation of 2S albumins via gel filtration

The 12 ml of solution from the previous step was passed over a Sephadex G-S0 medium (Pharmacia) column in two batches of 6 ml. The column was 2.5 cm in diameter, 100 cm in length, and run at a flow rate of approximately 27 ml/hr in 0.5M NaCl. Fractions of approximately 7 ml were collected. The fractions were monitored for the protein in two ways. First, total protein was detected by applying 10 μl of each fraction on a piece of Whatman 3MM paper, indicating the fraction numbers with a pencil. The spots are dried for 1 min in warm air and the proteins fixed by a quick (30 sec) immersion of the paper sheet in a 10% TCA solution. The sheet is then transferred to a Commassie Blue solution similar to that used for polyacrylamide gel staining. After 1 min, the paper is removed and rinsed with tap water. Protein containing fractions show a blue spot on a white background. The minimum detection limit of the technique is about 0.05 mg/ml. Those fractions containing protein were assayed for the presence of 2S albumins by adding 2 μl of the 7 ml fraction to 10 μl of sample buffer and then loading 6 μl of this mixture on a 17.5% polyacrylamide minigel. Those fractions shown to contain 2S albumins were pooled; the total volume of the pooled fractions was 175 ml.

Desalting of the isolated 2S albumins

This was done via HPLC over a $C_4$ column 25 cm in length and 0.46 cm in diameter (Vydac 214TP54, pore size 300 angstrom, particle size 5 μm). The HPLC equipment consisted of 2 pumps (model 510), a gradient controller (model 680) and an LC spectrophotometer detector (Lambda-Max model 481, all from Waters, Milford, Mass., U.S.A.). 21 ml of the 175 ml were loaded on this system in 6 runs of 3.5 ml each. The gradients were run as follows: Solution A was 0.1% TFA in $H_2O$, solution B 0.1% TFA in 70% $CH_3CN$. For 5 minutes, a solution of 0% B, 100% A was run over the column, after which the concentration of B was raised to 100% in a linear fashion over 70 minutes. During each run the 2S albumin fraction was collected, and after all 6 runs these fractions pooled and divided into 3 tubes, each of which therefore contained 7/175 of the 2S albumins from the 2.11 g seeds. Each of the aliquots was processed further separately and used for quantitative estimation of yields.

Trypsin Digest

Prior to digestion with trypsin the three aliquots were oxidized as described above. The trypsin digest was carried out essentially as described above. 0.95 ml of 0.1M Tris-HCl pH 8.5 was added to each aliquot, which was supplemented with 50 μg of trypsin (Worthington) and the reaction allowed to proceed for 4 hr at 37° C.

Isolation of the YGGFLK peptide

The enkephalin peptide containing the carboxyl terminal lysine residue was isolated using two sequential HPLC steps. As described in the small scale isolation procedure above, a peptide of the same sequence as that expected was synthesized and run over an HPLC system using the same column and gradient conditions described in the desalting step above. The retention time of the synthetic peptide was determined (FIG. 17A). The three trypsin digests were then (separately) loaded on the same column and the material with the same retention time as that of the synthetic peptide collected (the hatched area in FIG. 17B) and dried. The same procedure was then followed using the same equipment and gradients except that a C18 column (25×0.46 cm, Vydac 218TP104 material of pore size 300 angstrom and particle size 10 μm) was used. Again material with the same retention time as the synthetic peptide was collected (FIGS. 18A and 18B). This resulted in three preparations each derived from 7/175 of the total 2S albumin.

1/20 of the material in one of these three aliquots was used to check the sequence of the isolated peptide. This was determined by automated gas-phase sequencing using an Applied Biosystems Inc. (U.S.A.) 470A gas-phase sequenator. The stepwise liberated phenylthiohydantoin (PTH) amino acid derivatives were analyzed by an on-line PTH-amino acid analyzer (Applied Biosystems Inc. 120A). The sequenator and PTH-analyzer were operated according to the manufacturer's instructions. The HPLC-chromatograms of the liberated PTH-amino acids from cycles 1 through 6 are shown in FIG. 19. The sequence was as expected YGGFLK. The yield of PTH-amino acid of the first cycle was used for calculate the yield of this intermediate peptide (251–277 nmol/gr seed).

Removal of the extra Lysine from the enkephalin

The three aliquots resulting from the previous step were resuspended in 100 μl of 0.2M N-Ethylmorpholine pH 8.5 (Janssen Chimica, Belgium) and one third of each treated with 0.2 μg of carboxypeptidase B (Boehringer Mannheim, sequencing grade) at 37° C. The three aliquots were treated for 5, 12, and 17 minutes respectively, but all three digests proved to be equally effective. After digestion the enkephalin was purified by HPLC using the same equipment, column, and gradients as described under desalting above.

The final yield of enkephalin was determined by doing an amino acid analysis. An aliquot representing 1/150 of the total amount of the above mentioned three aliquots was hydrolyzed in 400 μl of 6N HCl, 0.05% phenol at 110° C. for 24 h. The hydrolysate was dried and amino acids derivitised into phenylthiocarbamoyl (PTC) residues (Bildingmeyer et al., 1984). Three separate aliquots of the PTC residue mixture were quantified using the PICO-TAG amino acid analysis system (Waters, Millipore, Milford, Mass., U.S.A.). Yields of enkephalin peptide were calculated for each of the three samples using alpha amino-butyric acid as an internal standard. Based on an average of the three determinations a final yield of 206 nmol enkephalin/g seed was calculated.

The identity of the peptide finally obtained was verified in three ways. First, its amino acid composition, which showed molar ratios of Gly, 1.76; Tyr, 1.00; Leu, 1.15 and Phe, 102. Secondly, its retention time on a reversed phase HPLC column match that of a reference enkenephalin peptide (FIG. 20) and finally its amino acid sequence was determined. These criteria unambiguously identify the peptide isolated from chimeric 2S albumins as being Leu-enkephalin.

EXAMPLE III

As a third example of the method described, a procedure is given for the production of two growth hormone releasing factor (GHRF) analogs. Synthetic and natural analogs of the originally isolated 44 amino acid peptide (Guillemin et al., 1982) in which the methionine at position 27 has been replaced by a leucine and in which the carboxyl terminus is modified in various ways or even shortened by four amino acids have been shown to be active (Kempe et al., 1986; Rivier et al., 1982). In this case two different analogs, designated hereafter as GHRFL and GHRFS, are produced. Both cases incorporate the substitution of leucine for methionine at position 27. GHRFL is produced in such a way that the carboxyl terminus is Leu-$NH_2$, as is found in a natural form of the peptide (Guillemin et al., 1982). GHRFS ends in Arg-Hse-$NH_2$, where Hse stands for homoserine. This analog was shown to be biologically active by Kempe et al. (1986). Both analogs are flanked by methionine codons in the 2S albumin so that they can be cleaved out by treatment with CnBr. This is possible as neither analog contains an internal methionine. After isolation of the two peptides using HPLC techniques they are chemically modified to result in the Leu-NH$_2$ and Arg-Hse-NH$_2$ carboxyl termini.

A set of synthetic oligonucleotides encoding the two GHRF analogs and CnBr cleavage sites are substituted of essentially the entire hypervariable region in a genomic clone encoding the 2S albumin of *Arabidopsis thaliana*. Only a few amino acids adjacent to the sixth and seventh cysteine residues remained. This chimeric gene is under the control of its natural promoter and signal peptide. The process and constructions are diagrammatically illustrated in FIGS. 21 and 22. The entire construct is transferred to tobacco, *Arabidopsis thaliana* and *Brassica napus* plants using an Agrobacterium mediated transformation system. Plants are regenerated, and after flowering the seeds are collected and the 2S albumins purified. The GHRF peptides are cleaved from the 2S albumin using the CnBr which cleavage site is built into the oligonucleotide, and then recovered using HPLC techniques.

Cloning of the *Arabidopsis thaliana* 2S albumin gene

The *Arabidopsis thaliana* gene has been cloned according to what is described in Example II (see also Krebbers et al., 1988). As already of record, the plasmid containing said gene is called pAT2S1. The sequence of the region containing the gene, which is called AT2S1, is shown in FIG. 13.

2. Deletion of the hypervariable region of AT2S1 gene and replacement by an AccI site Part of the hypervariable region of AT2S1 is replaced by the following oligonucleotide:

```
5'-CCA ACC TTG AAA GGT ATA CAC TTG CCC AAC-3' 30-mer
    P   T   L   K  G    I   H   L   P   N
``` in which the underlined sequences represent the AccI site and the surrounding ones sequences complementary to the coding sequence of the hypervariable region of the Arabidopsis 2S albumin gene to be retained. This results finally in the amino acid sequence indicated under the oligonucleotide.

The deletion and substitution of part of the sequence encoding the hypervariable region of AT2S1 is done using site directed mutagenesis with the oligonucleotide as primer. The system of Stanssens et al. (1987) is used as described in example I The individual steps of the process are as follows:

Cloning of the HindIII fragment of pAT2S1 containing the coding region of the AT2S1 gene into pMa5–8 (I). This vector carries on amber mutation in the $Cm^R$ gene and specifies resistance to ampicillin. The resulting plasmid is designated pMacAT2S1 (see FIG. 21 step 1).

Preparation of single stranded DNA of this recombinant (II) from pseudoviral particles.

Preparation of a HindIII restriction fragment from the complementary pMc type plasmid (III). pMc-type vectors contain the wild type $Cm^R$ gene while an amber mutation is incorporated in the Ap resistance marker.

Construction of gap duplex DNA (hereinafter called gdDNA) gdDNA (IV) by in vitro DNA/DNA hybridization. In the gdDNA the target sequences are exposed as single stranded DNA. Preoperative purification of the gdDNA from the other components of the hybridization mixture is not necessary.

Annealing Of the 30-met synthetic oligonucleotide to the gdDNA (V).

Filling in the remaining single stranded gaps and sealing of the nicks by a simultaneous in vitro Klenow DNA polymerase I/DNA ligasereaction (VI).

Transformation of a mutS host, i.e., a strain deficient in mismatch repair, selecting for Cm resistance. This results in production of a mixed plasmid progeny (VII).

Elimination of progeny deriving from the template strand (pMa-type) by retransformation of a host unable to suppress amber mutations (VIII). Selection for Cm resistance results in enrichment of the progeny derived from the gapped strand, i.e., the strand into which the mutagenic oligonucleotide has been incorporated.

Screening of the clones resulting from the retransformation for the presence of the desired mutation. The resulting plasmid containing the deleted hypervariable region of AT2S1 is called pMacAT2S1C40 (see FIG. 21 step 2).

3. Insertion of sequences encoding GHRF into the AT2S1 gene whose sequences encoding the hypervariable region have been deleted As stated above when the sequences encoding most of the hypervariable loop were removed an AccI site was inserted in its place. The sequences of interest will be inserted into this AccI site, but a second AccI site is also present in the HindIII fragment containing the modified gene. Therefore the NdeI-HindIII fragment containing the modified gene is subcloned into the cloning vector pBR322 (Bolivar, 1977) also cut with NdeI and HindIII. The position of the NdeI site in the 2S albumin gene is indicated in FIG. 4. The resulting subclone is designated pBRAT2S1 (FIG. 21, step 3). Sequences encoding the two versions of the growth hormone are inserted into the AccI site of pBRAT2S1 by constructing a series of complementary synthetic oligonucleotides which when annealed, form the complete sequence of the GHRF. The codon usage was chosen to approximately match that of AT2S1, a restriction site (StyI) to be used for diagnostic purposes was included, and at the ends of the GHRF encoding sequences staggered ends complementary to BamHI and PstI sites were included, along with extra bases to ensure that after the steps described below, the reading frame of the 2S albumin gene would be maintained. The eight oligonucleotides used in the two constructions are shown in FIG. 22. In FIG. 22A the limits of the oligonucleotides are indicated by the vertical lines, and the numbers above and below the sequence indicate their numbers. In oligonucleotides 4 and 8 the bases enclosed in the box are excluded, resulting in the GHRFS version of the construction. The bases marked by an * in FIG. 22A were found to have mutated to a T in the clone used for the further construction of GHRFL (pEK7), but as these changes did not effect the amino acid sequence the changes were not corrected. The peptide sequence of the GHRF peptide and the methionines included to provide CnBr sites are shown above the DNA sequence. The overhanging bases at each end serve to ligate the fragments into BamHI and PstI sites. These are removed by the S1 digestion. The blunt end fragment is then ligated into the Klenow treated AccI site of pBRAT2S1 as shown in FIG. 22B. The reading frame context of the AccI site is shown in the upper part of the figure, the cleavage sites being indicated by a '. The results of the manipulation are below, with the bases resulting from the AccI site and its filling in shown in bold type.

All six oligonucleotides used in each construction were kinased. For the annealing reaction 2 pmole of each oligonucleotide were combined in a total volume of 12 μl. The mixture was incubated at 90° C. for 10 min, moved to at temperature of approximately 65°–70° C. for 10 min, and then allowed to cool gradually to 30°–35° C. over a period of 30–45 min. At the end of this period ligase buffer (Maniatis et al., 1982) and 1.5 units of T4-ligase were added, the volume adjusted to 15 μl and the mixture incubated overnight at 16° C. The mixture was then incubated at 65° C. for 5 min after which 2.5 μl of 100 mM NaCl restriction endonuclease buffer (Maniatis et al., 1982), 5–10 units each of BamHI and PstI added, and the volume adjusted to 25 μl. This digest is to cleave any concatemers which have formed during the ligation step. After digestion for 45 min the reaction was extracted with phenol/chloroform, precipitated, and resuspended in 10 μl, 5 μl of which were ligated with pUC18 (Yanisch-Perron et al., 1985) which had been digested with BamHI and PstI and treated with bacterial alkaline phosphatase. After transformation of bacterial cells by standard techniques (Maniatis et al., 1982), recombinant colonies were screened by the method of Grunstein (1975) using oligonucleotide number 1 end labeled with $^{34}$P. Clones from each version of the GHRF gene were sequenced, and one clone for each version, designated pEK7 (containing GHRFL) and pEK8 (containing GHRFS) were used in further steps (See step 4 in FIG. 21).

The BamHI-PstI fragments of pEK7 and pEK8 were inserted into the AccI site of pBRAT2S1 (FIG. 21, step 5). The details of the treatments done to maintain the open reading frame are shown in FIG. 22. pEK7 and pEK8 were each cut with both BamHI and PstI, treated with S1 nuclease, and the fragments containing the GHRF encoding sequences isolated after gel electrophoresis. These fragments were then separately ligated with pBRAT2S1 which had been cut with AccI and treated with the Klenow fragment of DNA polymerase I. The resulting clones were checked for the appropriate orientation of the GHRF encoding sequences by digestion with StyI, a site for which had been included in the synthetic sequences for this purpose, and HindIII. Several clones which proved to contain inserts in the correct orientation were sequenced. The latter is necessary because S1 nuclease digestion cannot always be strictly controlled. One clone for each of two GHRF constructions confirmed to have the correct sequence was used in further steps. These were designated pEK100 and pEK200 for GHRFL and GHRFS respectively.

4. Reconstruction of the complete modified AT2S1 gene with its natural promoter

The complete chimeric gene is reconstructed as follows (see FIG. 21): The clone pAT2S1Bg contains a 3.6 kb BglII fragment inserted in the cloning vector pJB65 (Botterman et al., 1987) which encompasses not only the 1.0 kb HindIII fragment containing the coding region of the gene AT2S1 but sufficient sequences upstream and downstream of this fragment to contain all necessary regulatory elements for the proper expression of the gene. This plasmid is cut with HindIII and the 5.2 kb fragment (i.e., that portion of the plasmid not containing the coding region of AT2S1) is isolated. The clone pAT2S1 is cut with HindIII and NdeI and the resulting 320 bp HindIII-NdeI fragment is isolated. This fragment represents that removed from the modified 2S albumin in the construction of pBRAT2S1 (step 3 of FIG. 21) in order to allow the insertion of the oligonucleotides in step 5 of FIG. 21 to proceed without the complications of an extra AccI site. These two isolated fragments are then ligated in a three way ligation with the NdeI-HindIII fragments from pEK100 and pEK200 respectively (FIG. 21, step 6) containing the modified coding sequence. Individual transformants can be screened to check for appropriate orientation of the reconstructed HindIII fragment within the BglII fragment using any of a number of sites. The resulting plasmids pEK502 and pEK6011 consist of a 2S albumin gene modified only in the hypervariable region, surrounded by the same flanking sequences and thus the same promoter as the unmodified gene, the entirety contained on a BglII fragment.

5. Transformation of plants

The BglII fragment containing the chimeric gene is inserted into the BglII site of the binary vector pGSC1703A (FIG. 16) (see also FIG. 21 step 6), used and described in section 3 of example 2. The resultant plasmid is designated pTAD12. Using standard procedures (Deblaere et al., 1987), pTAD12 is transferred to the Agrobacterium strain C58C1Rif carrying the plasmid pMP90, also used in section 3 of Example II. This Agrobacterium is then used to transform plants. Tobacco plants of the strain SR1 are transformed using standard procedures (Deblaere et al., 1987). Calli are selected on 100 ug/ml kanamycin, and resistant calli used to regenerate plants.

The techniques for transformation of *Arabidopsis thaliana* and *Brassica napus* are such that exactly the same construction, in the same vector, can be used. After mobilization to *Agrobacterium tumefaciens* as described herebove, the procedures of Lloyd et al., (1986) and Klimaszewska et al. (1985) are used for transformation of Arabidopsis and Brassica respectively. In each case, as for tobacco, calli can be selected on 100 μg/ml kanamycin, and resistant calli used to regenerate plants.

In the case of all three species at an early stage of regeneration the regenerants are checked for transformation by inducing callus from leaf on media supplemented with kanamycin (see also point 6).

6. Screening and analysis of transformed plants

In the case of all three species, regenerated plants are grown to seed. Since different transformed plants can be expected to have varying levels of expression ("position effects", Jones et al., 1985), more than one tranformant must initially be analyzed. This can in principle be done at either the RNA or protein level. In this case seed RNA was prepared as described in Beachy et al., 1985 and northern blots carried out using standard techniques (Thomas et al., 1980). Since in the case of both Brassica and Arabidopsis of the entire chimeric gene would result in cross hybridization with endogenous genes, oligonucleotide probes complementary to the insertion within the 2S albumin were used; one of the oligonucleotides as used to make the construction can be used. For each species, i or 2 individual plants were chosen for further analysis as disclosed below.

First the copy number of the chimeric gene is determined by preparing DNA from leaf tissue of the transformed plants (Dellaporta et al., 1983) and probing with the oligonucleotide used above.

7. Isolation of GHRF analogs

A) Purification of the chimeric 2S albumins

The 2S albumins are i purified by high salt extraction, gel-filtration and reversed-phase HPLC as described in example II.

The correct elution times of the chimeric 2S albumins are determined by immunological techniques using commercially available (UCB-Bioproducts, Drogenbos, Belgium) antibodies directed against the natural GHRF.

B) Cleavage of the chimeric 2S albumin and isolation of the GHRF analogs

The desalted HPLC- purified GHRF containing 2S albumins are then treated with CNBr (Gross and Witkop, 1961).

CnBr will liberate the GHRF analogs with an extra homoserine/homoserine-lactone still attached to the COOH-terminus. The GHRF analogs are purified using classical reversed phase HPLC techniques, as described in Example II, and their amino acid sequence is determined using the method described in Example II.

The isolated GHRFS analog are amidated using ammonia, n-butylamine and n-dodecylamine as described by Kempe et al., 1986. This results in the described Arg-Hse-$NH_2$ terminus.

The second analog, GHRFL, with an extra methionine still present at the carboxyl terminus, is first treated with carboxypeptidase B, removing the carboxyl terminal homoserine residue (Ambler, 1972). This results in a Leu-Gly-COOH terminus. Treatment with the D-amino acid oxidase in the presence of catalase and ascorbate, as described in Kreil (1984), converts the glycine-COOH terminal into the terminal amide-$CONH_2$ and glyoxylic acid. This set of enzymatic steps results in the final amidated GHRFL analog.

The examples have thus given a complete illustration of how 2S-albumin storage proteins can be modified to incorporate therein an insert encoding Leu enkephalin or the Growth Hormone Releasing Factor followed by the transformation of tobacco, Arabidopsis and Brassica cells with an appropriate plasmid containing the corresponding modified precursor nucleic acid, the regeneration of the transformed plant cells into corresponding plants, the culture thereof up to the seed forming stage, the recovery of the seeds, the isolation therefrom of the hybrid 2S albumin and finally recovery the Leu-enkephalin or the GHRF from said hybrid protein in a purified form.

It will readily be appreciated that the invention thus provides a breakthrough in the art of genetically engineering proteins or polypeptides and of producing them in considerable amounts under conditions yielding them in a configuration that comes close to their natural ones.

It goes without saying that the invention is not limited to the above examples. The person skilled in the art will in each case properly select the storage proteins to be used for the production of any determined polypeptide or peptide of interest, the nature thereof, e.g. depending the adequate restriction sites which it contains in order to accommodate at best the corresponding DNA insert, the choice of the most suitable the seed specific promoter depending on the nature of the seed forming plant to be transformed for the sake of producing the corresponding hybrid protein from which the peptide of interest can ultimately be cleaved, recovered and purified.

There follows a list of bibliographic references which have been referred to in the course of the present disclosure to the extent when reference has been made to known methods for achieving some of the process steps referred to herein or to general knowledge which has been established prior to the performance of this invention.

It is further confirmed that plasmid pGV2260 has been deposited with the DSM on 2799 on December, 1983.

plasmid pSOYLEA has been deposited with the DSM on 4205 on Aug. 3, 1987; and plasmid pBN 2S1 has been deposited with the DSM on 4205 on Aug. 3, 1987.

plasmids pMa5-8 have been deposited with the DSM on 4567 and pMc on 4566 on May 3, 1988.

plasmid pAT2S1 has been deposited with the DSM on 4879 on Oct. 7, 1988 plasmid pAT2S1Bg has been deposited with the DSM on 4878 on Oct. 7, 1988 plasmid pGSC1703A has been deposited with the DSM on 4880 on Oct. 7, 1988 plasmid pEK7 has been deposited with the DSM on 4876 on Oct. 7, 1988.

plasmid pEK8 has been deposited with the DSM on 4877 on Oct. 7, 1988.

nowithstanding the fact that they all consist of constructs that the person skilled in the art can reproduce them from available genetic material without performing any inventive work.

REFERENCES

Altenbach, S. B., Pearson, K. W., Leung, F. W., Sun, S. S. M (1987) Plant Mol. Biol. 8, 239–250.

Ambler, R. P. (1972) Methods in Enzym. 25, 143–154.

Ampe C., Van Damme, J., de Castro, L. A. B., Sampaio, M. J. A. M., Van Montagu, M. and Vandekerckhove, J. (1986) Eur. J. Biochem. 159, 597–604.

Bassβüβner, R., Huth, A., Manteuffel, R., Rapaport, T. A., (1983), Eur. J. Biochem. 133, 321–326.

Beachy, R. N., Chen, Z.-L., Horsch, R. B., Rogers, S. G., Hoffman, N. J. and Fraley, R. T. (1985) EMBO J. 4, 3047–3053.

Benton, W. D. and Davis, R. W. (1977) Science 196, 180–182.

Bergman, L. W. and Kuehl, W. N. (1979) J. Biol. Chem. 254, 5690–5694.

Bildingmeyer, B. A., Cohen S. A. and Tarwin T. L. (1984) J. of Chromatography 336, 93–104.

Blobel, (1980) Proc. Natl. Acad. Sci. 77, 1496–1500.

Bolivar, F., Rodriguez, R. L., Greene, P. J., Betlach, M. C., Heynecker, H. L., Boyer, H. W., Crosa, J. H. and Falkow, S. (1977) Gene 2, 95.

Botterman, J. (1986) PhD. Thesis, State University of Gent.

Botterman, J. and Zabeau, M. (1987) DNA 6, 583–591.

Brown, J. W. S., Wandelt, Ch., Maier, U., Dietrich, G., Schwall, N., and Feix, G. (1986) EMBO workshop "Plant Storage protein Genes" program and abstract page 17, Eds. J. Brown and G. Feix, University of Freiburg, 1986.

Chee, P. P., Klassy, R. C. and Slightom, J. L. (1986) Gene 41, 47–57.

Chrispeels, N. J. (1983) Planta 158, 140–152.

Colquhoun, D. (1973) in Drug Receptors, Ed. Rang, H. P. (University Park Press, Baltimore, Md.) pp. 149–182.

Craig, S. and Goodchild, D. J. (1984) Protoplasma 122, 35–44.

Crouch, M. L., Tembarge, K. M., Simon, A. E. and Ferl, R. (1983) J. Mol. Appl. Gen. 2, 273–283.

De Blasts, R., Reynaerts, A., Hofte, M., Hernalsteens, J.-P., Leemans, J. and Van Montagu, M. (1987) Methods in Enzymology (in press). (Still in press E. K. ?)

De Castro, L. A. B., Lacerada, Z., Aramayo, R. A., Sampaio, M. J. A. M. and Gander, E. S. (1987) Mol. Gen. Genet. 206, 338–343.

Dellaporta S. L.; J.; Wood, J. and Hicks, B. (1983) Plant Molecular Biology Reports 1, 19–21.

De Wit, J. L. (1978) PhD thesis on: Nuclear Magnetic Resonance of Tobacco Mosaic Virus, Landbouwhogeschool Wageningen, The Netherlands, pp. 72–85.

Ellis, J. R., Shirsat, A. H., Hepher, A., Yarwood, J. N., Gatehouse, J. A., Croy, R. R. D. and Boulter, D. (1988) Plant Molecular Biology 10, 203–214.

Engvall, E. and Pesce, A. J. (1978) Scand. Immunol. Suppl. 7.

Ericson, M. L., Rodin, J., Lenman, M., Glimeliums, K., Lars-Goran, J. and Rak, L. (1986) J. Biol. Chem. 261, 14 576–14 581.

Fromm, . . . , Taylor, W. and Walbot, V. (1985) Proc. Natl. Acad. Sci. 82, 5824–5828.

Goldberg, R. B., Hoschek, G., and Vodkin, L. O. (1983) Cell 33, 465–475.

Greenwood, J. S. and Chrispeels, M. J. (1985) Plant Physiol. 79, 65–71.

Gross, E. and Witkop, B. (1961) J. of Amer. Chem. Soc. 83, 1510–1511.

Grunstein, M. and Hogness, D. (1975) Proc. Natl. Acad. Sci. 72, 3961.

Gubler, U. and Hoffman, B. J. (1983) Gene 25, 263–269.

Guillemin, R., Brazeau, P., Bββhlen, P., Esch, F., Ling, N. and Wehrenberg, W. B. (1982) Science 21, 585–587.

Harris, B. and Dure, L. (1981) Biochemistry 17, 3250–3256.

Herman, E. M., Shannon, L. M. and Chrispeels, M. J. (1986) In Molecular Biology of Seed Storage Proteins and Lectins, L. M. Shannon and M. J. Chrispeels Eds., American Society of Plant Physiologists.

Higgins, T. J. V. (1984) Ann. Rev. Plant Physiol. 35, 191–221.

Higgins, T. J. V., Llewellyn, D., Newbigin, E. and Spencer, D. (EK ? Symposium ref.+date).

Hirs, C. H. W. (1956) J. Biol. Chem. 219, 611–621.

Hoffman, L. M., Donaldson, D. D., Bookland, R., Rashka, K., Herman, E. M. (1987) EMBO J. 6, 3213–3221.

Hollenberg, C. P., Roggenkamp, R., Reipen, G. and Bielefeld, M. (1985) In: "Quo Vadis" Therapeutic agents produced by genetic engineering. Ed.: Joyeaux, A., Leygue, G., Morre, M., Roncucci, R. and Schmelck, R. P. H. SANOFI Recherche, Montpellier, France 65–78.

Horsch, R. B., Fry, J. E., Hoffmann, N. L., Eichholtz, D., Rogers, S. G. and Fraley, R. T. (1985) Science 227, 1229–1231.

Hughes, J., Smith, T., Morgan, B. and Fothergill, L. (1975a) Life Sci. 16, 1753–1758.

Hughes, J., Smith, T. W., Kosterlitz, H. W. Fothergill, L. A., Morgan, B. A. and Morris, H. R. (1975b) Nature 258, 577–579.

Hunt, L. T. and Dayhoff, M. O. (1976) in Atlas of Protein Sequence and Structure, ed. Dayhoff, M. O. National Biomedical Research Foundation, Silver spring, Md. Vol. 5, Suppl. II, pp. 113–145.

Jagodzinski, L., Sargent, T., Yang, M., Glackin, C., Bonner, J. (1987) Proc. Natl. Acad. Sci. USA. 78, 3521–3525.

Jekel, P. A., Weijer, W. J. and Beinkema, J. J. (1983) Anal. Biochem. 134, 347–354.

Jones J. D. G.; Dunsmuir, P. and Bedbrook, J. (1985) EMBO J. 4 (10), 2411–2418.

Josefsson, L-G.; Lenman, M., Ericson, M. L. and Rask, L. (1987). J. Biol. Chem. 262 (25), 12196–12201.

Jung, G., Jβüβner, F., Chem. Ztg. 96 (11), 603–611.

Kempe, T.; Chow, F., Peterson, S. M., Baker, P., Hays, W., Opperman, G., L'Italian, J. J., Long, G. and Paulson, B. (1986) Bio/Technology 4, 565–568.

Klimaszewska, K. and Keller, W. A. (1985) Plant Cell Tissue Organ Culture, 4, 183–197.

Kollman, V. H., London, R. E., Hanners, J. L., Gregg, C. T., Whaley, T. W., J. Labelled Compd. Radiopharm. 16 (6), 833–842.

Koncz, C. and Schell, J. (1986) Mol. Gen. Genet. 204, 383–396.

Krebbers, E., Herdies, L., De Clercq, A., Seurinck, J., Leemans, J., Vandamme, J., Segura, M., Gheysen, G., Van Montagu M. and Vandekerckhove, J. (1988) Plant Physiol. 87 (4), 859–866.

Kreil, G. (1984) Methods in Enzymology 106, 218–223.

Laemmli, U.K. (1970) Nature 227, 680–685.

Land, H., Grez, M., Hauser, H., Lindenmaier, W. and Schuetz, G. (1981) Nucl. Acids. Res. 9, 2251–2266.

Larkins B. A. and Hurkman, W. J. (1978) Plant Physiol. 62, 256–263.

Lewis, R. V., Stein, S. and Udenfriend, S. (1979) Int. J. Peptide Protein Res. 13, 493–497.

Lloyd, A. M., Barnason, A. R., Rogers, S. G., Byrne, M. C., Fraley, R. T. and Horsh, R. B. (1986) Science 234, 464–466.

Loenen and Blattner (1983) Gene 26, 171.

Lord, J. M. (1985). Eur, J. Biochem. 146, 403–409.

Maniatis, T., Fritsch, E. F. and Sambrook, J. (1982) Molecular Cloning. Cold Spring Harbor Laboratory, Cold Spring Harbor, New York.

Marris, C., Gallois, P., Copley, J. and Kreis, N. (1988) Plant Molecular Biology 10, 359–366.

Marton, L., Wullems, G. J., Molendijk, L. and Schilperoort, R. A. (1979) Nature, 277, 129–131.

Maxam, A. M. and Gilbert, W. (1980) Methods in Enzymology 65, 499–560.

Miller, J. K. and Barnes, W. M. (1986) Proc. Natl. Acad. Sci U.S.A. 83, 1026–1030.

Morinaga, T., Sakai, N., Wegmann, T., Tanaoki, T. (1983) Proc. Natl. Acad. Sci. 80, 4604–4606.

Ohtsuka, E., Matsuki, S., Ikehara, M., Takahashi, Y. and Matsubara, K. (1985) J. Biol. Chem. 260, 2605–2608.

Okamuro, J. K., Jofuku, K. D. and Goldberg, R. B. (1986) Proc. Natl. Acad. Sci. USA. 83, 8240–8244.

Okayama, H. and Berg, P. (1982) Mol. Cell. Biol. 2, 161–170.

Pasternak, G. W., Wilson, H. A. and Snyder, S. H. (1975) Mol. Pharmacol. 11, 340–350.

Perlman, D. and Halvorson, H. O. (1983) J. Mol. Biol. 167, 391–409.

Radke, S. E., Andrews, B. M., Moloney, M. M., Crouch, M. L. Kridl, J. C. and Knauf, V. C. (1988) Theor. Appl. Genet. 75, 685–694.

Rivier, J., Spiess, J., Thorner, M. and Vale, W. (1982) Nature 300, 276–278.

Roden, L. T., Miflin, B. J., Freedman, R. B. (1982) FEBS Lett. 138, 121–124.

Scofield, S. R. and Crouch, M. L. (1987) J. Biol. Chem. 262 (25), 12202–12208.

Seiringer, B. R., Liebisch, D. C., Gramsch, C., Herz, A., Weber, E., Evans, C. J., Esch, F. S. and Boehlen, P. (1985) Nature 313, 57–59.

Sengupta-Gopalan, C., Reichart, N. A., Barker, R. F., Hall, T. C. and Kemp, J. D. (1985) Proc. Natl. Acad. Sci. USA 82, 3320–3324.

Sharief, F. and Li, S. S. (1982) J. Biol. Chem. 257, 14753–14759.

Simantov, R. and Snyder, S. H. (1976) Life Sci. 18, 781–788.

Slightom, J. L. and Chee, P. P. (1987) Biotechn. Adv. 5, 29–45.

Stanssens, P., McKeown, Y., Friedrich, K., and Fritz, H. J. (1987) Manual EMBO Laboratory Course; 'Directed mutagenesis and protein engineering' held at Max Planck Institute fβüβr Biochemie, Martinsried, W-Germany, Jul. 4–18, 1987.

Staswick, P. E. (1988) Plant Physiol. 87, 250–254.

Takahashi, Y., Kato, Kikuya, Hayashizaki, Y., Wakabayashi, T., Ohtsuka, E., Matsuki, S., Ikehara, M. and Matsubara, K. (1985) Proc. Natl. Acad. Sci. U.S.A. 82, 1931–1935.

Thomas, P. S. (1980) Proc. Natl. Acad. Sci. 77, 5201.

Towbin, H., Staehelin, T. and Gordon, J. (1979) Proc. Natl. Acad. Sci. (U.S.A.) 76, 4350–4354.

Velten, J., Velten, L., Hain, R. and Schell, J. (1984) EMBO J. 3, 2723–2730

Walling, L. Drews, G. N. and Goldberg, R. (1986) Proc. Natl. Acad. Sci. 83, 2123–2127.

Yang, F., Luna, V. G., McAnelly, R. D., Noberhaus, K. H., Cupples, R. L., Bowman, B. H. (1985) Nucl. Acids Res. 13, 8007–8017.

Yanisch-Perron, C., Vieira, J. and Messing, J. (1985) Gene, 33, 103–119.

Youle, R. and Huang, A. H. C. (1981) American J. Bot. 68, 44–48.

TABLE 1

| 2S Albumin As % Of Total Seed Protein | |
|---|---|
| Family, species (common name) | % |
| Compositae | 62 |
| *Helianthus annuus* (sunflower) | |
| Cruciferae | 62 |
| *Brassica* spp. (mustard) | |
| Linaceae | 42 |
| *Linum usitatissimum* (linseed) | |
| Leguminosae | |
| *Lupinus polyphyllus* (lupin) | 38 |
| *Arachis hypogaea* (peanut) | 20 |

TABLE 1-continued

| 2S Albumin As % Of Total Seed Protein | |
|---|---|
| Family, species (common name) | % |
| Lecythidaceae | 30 |
| *Bertholletia excelsa* (brazil nut) | |
| Liliaceae | 27 |
| *Yucca* spp. (yucca) | |
| Euphorbiaceae | 44 |
| *Ricinus communis* (castor bean) | |

We claim:

1. An isolated DNA fragment comprising a seed-specific promoter region of an *Arabidopsis thaliana* gene coding for a precursor of a 2S albumin wherein said 2S albumin comprises an amino acid sequence selected from the group of AT2S1, AT2S2, AT2S3 and AT2S4 of FIG. 2A.

2. The isolated DNA fragment of claim 1, wherein said promoter region comprises a sequence of FIG. 13 from nucleotide position -431 to nucleotide position -1.

3. An isolated DNA fragment from plasmid pAT2S1Bg, deposited as DSM No. 4878, comprising a sequence of FIG. 13 from nucleotide position -431 to nucleotide position -1.

* * * * *